(12) United States Patent
Nakao

(10) Patent No.: US 7,588,557 B2
(45) Date of Patent: Sep. 15, 2009

(54) MEDICAL INSTRUMENT FOR FLUID INJECTION AND RELATED METHOD

(75) Inventor: Naomi L. Nakao, New York, NY (US)

(73) Assignee: Granit-Medical Innovations, LLC, New York, NY (US)

( * ) Notice: Subject to any disclaimer, the term of this patent is extended or adjusted under 35 U.S.C. 154(b) by 498 days.

(21) Appl. No.: 10/670,106

(22) Filed: Sep. 24, 2003

(65) Prior Publication Data

US 2005/0065483 A1 Mar. 24, 2005

(51) Int. Cl.
*A61M 5/178* (2006.01)
(52) U.S. Cl. .............................. 604/164.11; 604/164.01
(58) Field of Classification Search .................. 604/21, 604/93.01, 164.01, 164.09, 164.1, 164.11, 604/272, 264, 239, 117, 115, 158, 161, 164.03, 604/164.06, 164.13; 606/41, 110, 113
See application file for complete search history.

(56) References Cited

U.S. PATENT DOCUMENTS

| | | | |
|---|---|---|---|
| 2,097,039 A | 10/1937 | Peterson | |
| 4,411,657 A | 10/1983 | Galindo | |
| 4,838,877 A | 6/1989 | Massau | |
| 5,219,358 A | 6/1993 | Bendel et al. | |
| 5,279,542 A | 1/1994 | Wilk | |
| 5,304,120 A * | 4/1994 | Crandell et al. | 604/501 |
| 5,344,402 A | 9/1994 | Crocker | |
| 5,354,279 A * | 10/1994 | Hofling | 604/164.12 |
| 5,419,777 A | 5/1995 | Hofling | |
| 5,536,267 A * | 7/1996 | Edwards et al. | 606/41 |
| 5,921,999 A | 7/1999 | Dileo | |
| 6,217,554 B1 | 4/2001 | Green | |
| 6,231,591 B1 | 5/2001 | Desai | |
| 6,283,951 B1 | 9/2001 | Flaherty et al. | |
| 6,302,870 B1 | 10/2001 | Jacobsen et al. | |
| 6,358,258 B1 | 3/2002 | Arcia et al. | |
| 6,432,092 B2 | 8/2002 | Miller | |
| 6,482,178 B1 | 11/2002 | Andrews et al. | |
| 6,551,278 B1 | 4/2003 | Geitz | |
| 6,592,559 B1 | 7/2003 | Pakter et al. | |
| 6,730,061 B1 | 5/2004 | Cuschieri et al. | |
| 2002/0188275 A1 | 12/2002 | McGuckin, Jr. | |

* cited by examiner

*Primary Examiner*—Kevin C. Sirmons
*Assistant Examiner*—Elizabeth Moulton
(74) *Attorney, Agent, or Firm*—R. Neil Sudol; Henry D. Coleman; William J. Sapone

(57) ABSTRACT

A medical instrument for fluid injection includes a tubular member and a plurality of hollow needle elements connected to one end of the tubular member. Generally, the tubular member has a lumen and all the needle elements communicate with the lumen to enable a distribution of a diagnostic or therapeutic fluid to various points in a predetermined region. The tubular member is provided with a fluid introduction port at an end of the tubular member opposite the needle elements, the fluid introduction port communicating with the lumen. The needle elements are disposed in a predetermined configuration adapted to carry out a desired function. The needle elements are at least partially made of resilient material with a memory so that the needle elements are biased by their internal stresses towards a predetermined rest configuration and are alternately disposable in the rest configuration and at least one stressed or loaded configuration.

4 Claims, 14 Drawing Sheets

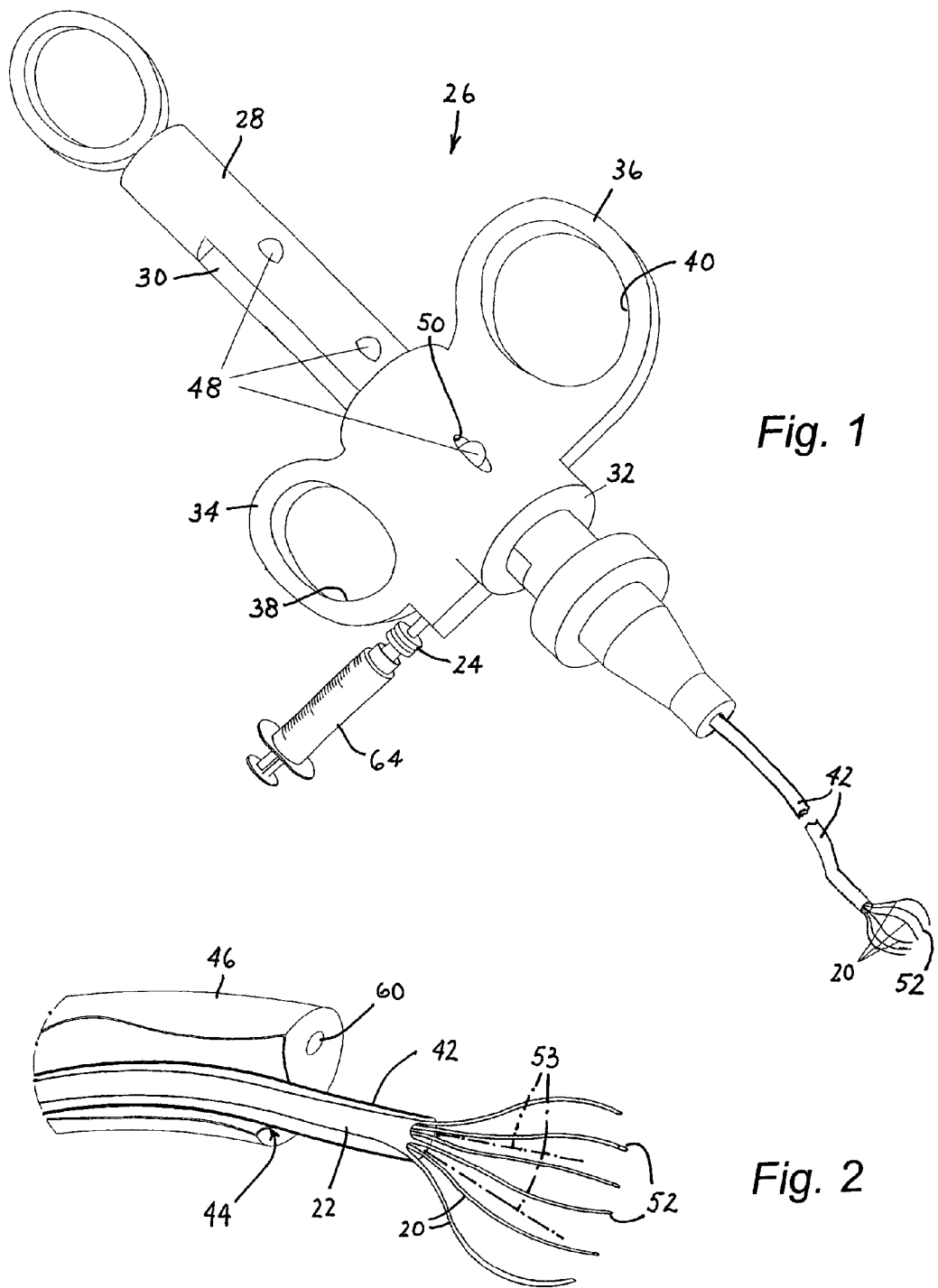

US 7,588,557 B2

MEDICAL INSTRUMENT FOR FLUID INJECTION AND RELATED METHOD

FIELD OF THE INVENTION

This invention relates to a surgical instrument for use in the application of a fluid to organic tissues. More specifically, this invention relates to such an instrument useful in the injection of fluid into organic tissues at multiple interspaced locations. The invention additionally relates to an associated method employing the instrument. The instrument may be used to inject a chemotherapeutic agent into a tumor or to facilitate the removal of certain types of lesions inside internal body cavities. The instrument may also be used in a method of treating bleeding ulcers or bleeding from other causes inside body cavities. In addition, the instrument may be used to treat gastro-esophageal reflux disorder (GERD). The instrument may be used moreover to inject anesthetics or other fluids into areas on the body surface for the purpose of administering local anesthesia, or other substances.

BACKGROUND OF THE INVENTION

In a conventional polyp removal operation, an endoscope is inserted into an internal cavity of a patient, e.g., into the colon, and is used to locate abnormal tissue growths such as precancerous polyps or cancers in the internal cavity. Upon locating a polyp, or another growth, which is to be removed, a surgeon or gastroenterologist extends a wire through a tube in the working channel of the endoscope and slides the wire in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to position the loop around the neck, or pedicle, of the polyp or growth. Once the loop is in contact with the neck of the polyp, electrical current is conducted through the loop via the wire. Generally, as the loop is closed over the base of the polyp, electrical current is transmitted through the narrowed organic tissue and thereby generates therein heat sufficiently great to cut and cauterize the polyp, ressecting it off the colon wall.

The above-described procedure is not difficult when the polyp has a neck, or a pedicle. However, if the polyp is flat or sessile, it is very difficult to grasp and surround it with the snare for adequate transection. Often the snare slides off the polyp, and in many cases the polyp has to be removed in a piecemeal fashion because the entire lesion cannot be snared at once. In addition, sessile polyp resection presents the danger of organ perforation. The wall of the colon is very thin. If successive burning takes place, the cautery current may burn through the wall of the colon, causing a perforation. This complication is life-threatening and requires immediate surgical intervention. This problem has been partially but inadequately addressed by injecting saline into an area or areas adjacent to the flat lesion. During this process, several injections are administered around the flat lesion. The injections are delivered through a very short stainless steel needle, the length of which is limited by the curves of the fiber optic instrument. This short needle is oftentimes insufficient to deliver the necessary amount of fluid. More often than not, the area surrounding the flat polyp is raised, essentially burying the polyp even deeper in the middle of the mounds of saline that are created. In the best-case scenario, the flat polyp ends up on top of a single large mound. This mound is smooth, slippery, and despite the fact that it is larger than the original lesion, it is still too flat to snare. The lesion to be removed does not have a narrow neck or pedicle to enable snaring, but does in fact have a base much broader than its body.

In another kind of surgical procedure, pertaining to internal bleeding, the patient has to be rushed to the operating room for resection of the part of the organ that is bleeding. More often than not the bleeding occurs through an artery, wherein the blood is pumped out rapidly, threatening imminent exsanguination and patient death. Attempts have been made to control such bleeding through use of the fiber optic endoscope. These attempts have been inadequate at best. One of the methods used to control such bleeding is injecting saline solution, or a mixture of saline and epinephrine (a vasoconstricting agent), around the bleeding site. The site is first washed off with water administered through a catheter introduced through the working channel of the endoscope. This catheter has then to be removed, and the mixture of water and blood is suctioned through the suction channel. A sheath housing a singular needle is then introduced, and an injection is made near the bleeding source. The endoscopist attempts to inject all around the bleeding source causing a mound or mounds to be raised around the bleeding vessel. This process takes a long time during which the patient continues to bleed. Saline and saline with epinephrine stay concentrated in one location in the tissue for two to three minutes, and then re-absorption into the systemic circulation occurs. This is not enough time to form an adequate clot and arrest the bleeding.

Another kind of procedure addressed herein pertains to gastro-esophageal reflux disease (GERD). This common problem affects one third of the population in the United States. Acid reflux is caused by a lax gastro-esophageal sphincter. The sphincter between the esophagus and the stomach is the natural barrier to acid refluxing up from the stomach into the esophagus. When this barrier malfunctions, acid freely splashes up and into the esophagus causing heartburn, esophageal inflammation, ulcerations, Barrett's Esophagus, esophageal cancer, and respiratory problems. Presently, GERD is treated with medications, which shut off acid production in the stomach. Most patients need to take this medication for a lifetime. Recently, a number of methods have been attempted to correct this problem through the fiber optic endoscope. An endoscopic sewing machine has been invented, with which pleats are created beneath the lax gastro-esophageal sphincter. This instrument is costly and difficult to use, has resulted in esophageal tearing and perforation, and has not been proven to cure GERD.

This disclosure also relates to the method of injecting anesthetics or other medications around a lesion on the body surface. When a patient comes to the emergency room to be treated for a laceration or a cut, before sewing this cut closed, a local anesthesia must be administered. This process is lengthy and painful: a series of singular injections into and along the wound site are administered, causing ostensibly similar discomfort than would occur with suturing the wound without the anesthetic. The same problem exists during resection of a local breast mass, lypoma, or other superficial lesions.

This disclosure also relates to the problem of injecting a tumor mass with a chemotherapeutic agent. If a single needle is used, numerous injections at different locations and depths of the tumor must be administered. This is traumatic, erratic, and frequently does not achieve the desired effect.

This invention also relates to the problem of having to insert a needle or another slim surgical instrument through the narrow biopsy channel of a fiber optic endoscope or laparoscope. The configurations that the endoscope must be capable of assuming necessarily imposes limitations on the shape of the surgical instrument.

OBJECTS OF THE INVENTION

It is a general object of the present invention to provide an improved medical instrument for the application of a fluid to internal body tissues of a patient.

It is another general object of the present invention to provide such an instrument that addresses one or more of the above-discussed problems.

Accordingly, an object of the present invention is to provide an instrument assembly and/or a related method of lifting a flat or sessile lesion in preparation for its removal from an internal body cavity.

A more specific object of the present invention is to provide an instrument assembly and/or a related method for creating an artificial neck or pedicle underneath a flat lesion in order to enable the grasping this lesion with a snare or other instrument for its removal.

Another, more particular object of the present invention is to provide an injection technique wherein the flat lesion is lifted off of the body cavity wall, creating a safe cushion where cutting may take place without the risk of perforation.

A more specific object of this invention is to provide a needle or needle assembly that can be introduced to great depths via an endoscope channel.

A further object of this particular invention is to provide an instrument assembly and/or an associated method for delivering a dye to identify the exact borders of a lesion, for example, for the purpose of marking the site of the lesion for subsequent follow-up examinations.

Another object of this invention is to provide such an instrument assembly which is easy to use and can accomplish the desired result in a short period of time, thereby reducing patient discomfort, morbidity, anesthesia requirement and staff and facility cost.

It is a further object of this invention to provide an instrument assembly and/or an associated injection technique for treating and arresting bleeding from inside a body cavity.

Yet another, more particular object of this invention is to spare the patient a lengthy and complicated operation to remove the organ part which is bleeding.

It is a further particular object of this invention is to provide a noninvasive technique to treat internal bleeding.

It is an additional object of the present invention to provide a safe, easy and quick way to treat gastro-esophageal reflux disease.

It is an additional particular object of this invention to spare the patient a lifetime of taking antacid medications or complicated and dangerous surgery.

It is a further object of this invention to provide an instrument that injects an anesthetic or another fluid along a wound or a lesion on the outer surface of the body.

An additional particular object of this invention is to spare the patient the pain of multiple injections around an already painful area.

Another object of the present invention is to provide such an instrument assembly which is either disposable or reusable.

An additional object of this invention is to provide an instrument assembly for injecting a tumor whereby the entire tumor mass can be infiltrated with the medicinal fluid in one injection procedure in a predictable and pre-calculated fashion.

Another object of the invention is to provide an endoscopic instrument that can be inserted into a body cavity through the lengthy and narrow channel of an endoscope in a particular configuration fitting through this channel, and once in the hollow body cavity can then be reformed into another shape necessary for the procedure to be performed.

These and other objects of the invention will be apparent from the drawings and descriptions herein. Although every object of the invention is deemed to have been met by at least one embodiment of the invention, there is not necessarily any one embodiment that achieves all of the objects of the invention.

SUMMARY OF THE INVENTION

A medical instrument for fluid injection comprises, in accordance with the present invention, a tubular member and a plurality of hollow needle elements connected to one end of the tubular member. Generally, the tubular member has a lumen and all the needle elements communicate with the lumen to enable a distribution of a diagnostic or therapeutic fluid to various points in a predetermined region. The tubular member is typically provided with a fluid introduction port at an end of the tubular member opposite the needle elements, the fluid introduction port communicating with the lumen.

The needle elements are disposed in a predetermined configuration relative to one another. The configuration of the needle element/s is adapted to carry out a desired function. For instance, the needle elements may be disposed in an axial symmetric array for enabling the injection of fluid into organic tissues in a circular area. Where the circular area is located about a pre-selected tissue mass such as a sessile lesion, the injection of fluid may serve to generate an artificial pedicle for facilitating a removal of the lesion in a cauterization snare procedure. Where the circular region is along a lumen of an organ, the injection of fluid may create an artificial sphincter. In another example, the needle elements may extend throughout a volume having a generally predetermined shape such as a sphere or an oblate spheroid. Such a needle configuration is conducive to delivering a liquid such as a chemotherapeutic agent throughout a target tissue mass such as a tumor. The needle elements may have different sizes and shapes. Preferably, one or more of the needle elements are provided along their lengths with a plurality of apertures allowing the introduction of fluid at numerous locations in the target tissue mass.

In accordance with another feature of the present invention, the needle elements are at least partially made of resilient material with a memory. The memory characteristic may function to define a rest configuration of the needle elements, the rest configuration being assumed by the needle elements in the absence of externally applied forces. Alternatively, the memory configuration may be triggered by environmental conditions, such as the temperature of the needle elements. Thus, the needle elements may have one unstressed configuration at temperatures below a predetermined activation temperature and another configuration (the "memory" configuration) above the activation temperature. The activation temperature is generally body temperature or a temperature not so much higher than body temperature that a patient's tissues would be burned or damaged.

Pursuant to the former memory function, the needle elements are biased by their internal stresses towards a predetermined rest configuration and are alternately disposable in the rest configuration and at least one stressed or loaded configuration. An example of a stressed configuration is an at least partially collapsed configuration whereby the needle elements may be disposed inside a biopsy channel of an endoscopic instrument for delivery to a surgical site inside a patient. The rest or unstressed configuration in this case is an at least partially opened or expanded configuration and the needle elements automatically assume the rest configuration upon an ejection of the needle elements from the endoscope biopsy channel.

Pursuant to the latter memory function, the needle elements may have a straight but flexible configuration facilitating insertion of the injection instrument into the patient's body, for instance, via the biopsy channel of a deployed endoscope. Upon the application of heat to the needle elements, they assume respective curved shapes. Where the needle elements are made of shape memory Nitinol or other electrically resistive material, the application of a voltage (monopolar or bipolar) to the needle elements will result in a temperature rise triggering a shape change to configurations built into the needle elements during the manufacturing process. The voltage may be applied to the needle elements via one or more conductors in the tubular member. Where the conductors are connected to the needle elements at only one end thereof (the proximal end), the patient's tissues complete a monopolar electrical circuit. The circuit is closed after the insertion of the distal ends of the needle elements into the patient's tissues. Generally, the density of electrical current conducted through the patient's tissues is so low that no damage results to the tissues.

Alternatively, electrical current may be applied to the needle elements prior to the injection thereof into the patient's tissues. In that case, where the injection instrument is disposed inside a larger needle member or catheter prior to deployment of the needle elements in the patient, electrical current may be transmitted through the needle elements from the tubular member to the larger needle or a conductor in the catheter. The needle elements start assuming their memory configurations immediately upon release from the larger needle or catheter or other delivery tool. It is to be noted that the heat or temperature activation of a material such as shape memory Nitinol may be useful for single needles, catheters, scalpels, and other medical instruments, as well as the multiple needle instruments discussed above.

For certain applications it is advantageous if the needle elements have an arcuate shape in the opened or expanded configuration. For instance, to generate an artificial pedicle under a sessile lesion, the needle elements are formed with a rest or expanded configuration in which they extend away from the one end of the tubular member and are convex on an outer side and concave on an inner side. In this embodiment of the fluid injection instrument, the needle elements together define a bulbous ovoid shape, with tips of the needle elements angled inwardly at a distal tip of the medical instrument. The needle elements may extend in an axially symmetric distribution.

In an embodiment of the fluid injection instrument designed for building an artificial gastro-esophageal or other sphincter, the needle elements extend away from the one end of the tubular member and are concave on an outer side and convex on an inner side so that the needle elements together define a grappling hook shape, with tips of the needle elements angled outwardly at a distal tip of the instrument.

In another embodiment the needle elements are substantially rigid and disposed in a fixed configuration relative to one another and relative to the tubular member. For example, the needle elements may be linear and disposed in parallel to one another in a planar forked configuration. Alternatively, the needle elements may each comprise a plurality of straight segments each disposed at an angle relative to an adjacent one of the segments. In this case, the needle elements may be disposed in a cup-shaped configuration relative to one another.

The tubular member and the needle elements may be disposed inside a second, outer tubular member such as a catheter. The catheter facilitates deployment of the fluid injection instrument via an endoscope, whether a flexible instrument such as a colonoscope or a rigid instrument such as a laparoscope.

In another, simpler embodiment, the flexible (Nitinol) needle is singularly disposed within the catheter. Because of its flexible nature it can be longer than the currently used short (2.5 mm) needles, and can traverse a convoluted Fiberoptic endoscope. The advantage of a longer needle is that the injection can be made into deeper tissue planes, or in the case of esophageal varices, can be performed obliquely.

In another embodiment similar to the above needle, a singular needle is provided, which has the memory of a curve set into it. When the needle is inside the catheter, the needle will be straight so it can be passed through the endoscope. Once advanced to exit the distal end of the endoscope, the needle assumes its curved configuration. This sort of needle is used for injection of places that need a curved needle such as esophageal varices that are situated at a right angle to the endoscope, or a difficult polyp located behind a fold in the colon. In the case of this curved needle, the distal end of the catheter would be provided with a short stainless steel "collar" that would contain the curved tip of the needle. This collar would protect the endoscope channel from being pierced or scratched by the needle when it is ejected.

A medical method in accordance with the present invention utilizes a tubular member having, at one end, a plurality of hollow needle elements. Distal tips of the needle elements are placed in contact with organic tissues of a patient. Thereafter a fluid is fed through the tubular member and through the needle elements to apply the fluid to the organic tissues at a plurality of spaced locations.

Where the method involves the application of the fluid to internal tissues or the patient, the needle elements and a distal end portion of the tubular member are inserted into the patient. In a minimally invasive procedure, the needles are preferably made at least partially of a resilient material with a memory, so that the needle elements may be inserted in at least partially collapsed configuration. After insertion of the needle elements into the patient, they are expanded from the collapsed configuration to an at least partially opened configuration. Subsequently, the distal tips of the needle elements are placed into contact the organic tissues.

In accordance with another feature of the present invention, the needle elements are placed in contact with the organic tissues around a pre-selected tissue mass. The fluid may then be injected to create a pedicle or neck below the tissue mass. To carry out this procedure, the needle elements are preferably distributed about a longitudinal axis of the distal end portion of the tubular member in the opened configuration. More preferably, the needle elements are arcuate and together define the opened or expanded configuration as a substantially bulbous ovoid shape with the distal tips being disposed in a circular array. The organic tissues are pierced and injected with fluid along a circular locus of points.

In accordance with another feature of the present invention, the needle elements are placed in contact with a lumen of an organ such as an esophagus, exemplarily for purposes of creating a sphincter. To carry out this procedure, the needle elements are distributed about a longitudinal axis of the distal end portion of the tubular member in the opened configuration and are concave on an outer side and convex on an inner side. The needle elements thus collectively define a grappling hook shape to facilitate the placing of the distal tips in contact with the lumen of the internal organ.

In another medical method in accordance with the present invention, a tubular member having, at one end, a plurality of hollow needle elements is manipulated so as to place distal tips of the needle elements in contact with organic tissues of a patient about a bleeding site. Thereafter a coagulant or other substance such as collagen is fed through the tubular member and through the needle elements to inject the substance into the organic tissues to stem the bleeding at the site.

A surgical instrument assembly for use in snare cauterization operations comprises, in accordance with a particular embodiment of the present invention, a plurality of needles interconnected to one main hollow metallic wire, the wire passing longitudinally through a tubular sheath member. The needle assembly is made of a metal with memory such as superelastic Nitinol. This needle assembly is collapsed inside the sheath prior to and during an insertion operation. A manually actuatable shifter is operatively connected to the wire for longitudinally sliding the wire along the sheath in alternately opposite directions. The hollow wire is proximally connected to a port, through which fluid gel can be injected. The plurality of needles is so designed that when ejected from the sheath, the needles curve medially or outwardly depending on the purpose of use.

During use, the needle assembly housed inside the sheath is introduced through the working channel of the endoscope. The plurality of interconnected needles is ejected from the sheath and is positioned around the lesion that is to be treated. If the lesion is a sessile polyp, the needles curved medially are positioned to substantially surround the polyp. Dye such as Indigo Carmine is injected to mark the boundaries of the polypoid lesion. The position of the needles can be fixed at any time by pushing a spring-operated button or buttons near the proximally located handle which locks the needles into the desired position. When the proper position is achieved, the needles are pushed into the tissue surrounding the lesion. As the assembly is pushed deeper, the circle created by the needle tips underneath the lesion becomes smaller. If necessary, the sheath may be pushed down partially enclosing the plurality of needles until the desired diameter of the circle created underneath the lesion is achieved. When the desired position is achieved, the needles may be locked into place with the button operable near the proximally located handle. Then, fluid is injected parallel to the lumen of the colon, raising the flat lesion off the mucosa, and creating an artificial pedicle. The needles may have lateral holes so that when the needles are inserted along the base of the polyp, not straight into the wall of the colon, but parallel to the wall, the injected fluid raises the whole breath of the polyp. The needle assembly is then removed in preparation of polyp resection with the cautery snare.

Pursuant to another feature of the present invention, the needle assembly may be used to inject a gel solution such as collagen around a bleeding ulcer crater with an artery in its midst. This process will arrest the bleeding quickly and efficiently and save the patient possible exsanguination or surgery.

In another specific embodiment of the present invention, the needles may be curved outwardly when in the ejected position. This embodiment may be used to treat gastro-esophageal reflux disease by injecting collagen or another long-lasting gel into, around or immediately below the gastro-esophageal sphincter, creating an artificial sphincter.

According to the present invention, the needle assembly may be formed by using a non-deformable metal such as stainless steel. This needle assembly may be used on the body surface in order to administer an anesthetic or other fluids or gels in one maneuver saving the patient the pain of multiple singular injections.

A medical instrument in accordance with the present invention includes a hollow needle element made of a resiliently deformable material, the needle element having a memory for assuming a use configuration different from an insertion configuration.

Pursuant to more specific features of the present invention, the needle element is manufactured to assume the use configuration upon attaining a predetermined activation temperature and is made of an electrically resistant material so that conduction of current through the needle element elevates the temperature thereof.

In a particular embodiment of the present invention, the needle element with the memory is one of a plurality of needle elements deployed from a distal end of a tubular member. The needle elements may all be connected to the distal end of the tubular member. In that case, fluid force fed through the tubular member is injected through the needle elements. Alternatively, the needle elements are all movably inserted into the tubular member and ejectable from the tubular member through at least one opening therein. In that event, the tubular member may take the form of a hollow needle carrier or delivery vehicle for the needle elements.

A surgical method comprises, in accordance with the present invention, providing an instrument having a first configuration at room temperature, inserting the instrument into a patient, thereafter heating the instrument to an activation temperature above room temperature, and automatically deforming the instrument to a second configuration different from the first configuration upon the attainment of the activation temperature by the instrument. The deforming of the instrument occurs by virtue of the attainment of the activation temperature. The method further includes using the instrument in the second configuration to perform an operation on internal body tissues of the patient and maintaining the instrument at a temperature of at least the activation temperature during the use of the instrument to perform the operation.

Pursuant to another feature of the present invention, the heating of the instrument includes conducting an electrical current through at least a portion of the instrument. Where the instrument is delivered to a surgical site in the patient via a catheter, the electrical current may be carried through at least one conductor extending along the catheter. Alternatively, at least one wire conductor may be connected to the instrument, the electrical current being conducted through at least one conductor extending along the catheter.

A medical instrument also comprises, in accordance with the present invention, an outer needle and a plurality of hollow inner needles disposed within the outer needle for ejection from the outer needle through at least one opening therein. At least one of the inner needles may have a memory for assuming a predetermined configuration upon ejection from the outer needle through one of the openings. If so, the one needle may be made of a heat-deformable material for assuming the predetermined configuration only upon attainment of a predetermined activation temperature. At least one electrical conductor may be operatively connected to the one needle for delivering an electrical current to the one needle.

Pursuant to another feature of the present invention, at least one of the plural needles is provided along at least a portion of its length with a plurality of spaced apertures or holes.

A related medical method comprises, in accordance with the present invention, providing a medical instrument having an outer needle and a plurality of hollow inner needles disposed within the outer needle, inserting a distal end portion of the outer needle into a target tissue mass, thereafter ejecting the inner needles from the outer needle through at least one opening therein so that the needles are distributed throughout at least a portion of the tissue mass, and subsequently injecting a fluid through the inner needles into the tissue mass to permeate or infiltrate at least the portion of the tissue mass with the fluid. In the case that the tissue mass is a tumor, the fluid may include a chemotherapeutic agent.

Where at least one of the inner needles has a memory, that needle has a first configuration inside the outer needle and the method further comprises reforming the one inner needle to assume a second configuration different from the first configuration upon ejection of the one inner needle from the outer needle and into the tissue mass.

Pursuant to a particular feature of this method, the memory is heat activated and the method additionally comprises applying electrical current to the one inner needle to heat that needle to an activation temperature triggering formation of the one inner needle into the second configuration.

A medical instrument in accordance with another feature of the present invention includes at least one needle element (e.g., a hollow needle for fluid injection) made of an electrically resistant material, the needle being preformed to assume a desired use configuration upon attainment of a predetermined activation temperature above room temperature.

The needle element may be one of a plurality of needle elements all operatively coupled to a tubular member and deployable from a distal end of the tubular member. In a specific embodiment of the invention, the tubular member is a hollow outer needle, while the needle elements are hollow, disposed in the outer needle, and ejectable from the outer needle through at least one opening therein. The instrument then further comprises at least one electrical conductor operatively connected to the one needle element for transmitting a current through that needle element to heat it to the activation temperature. In another specific embodiment of the present invention, the needle elements are connected to a distal end of the tubular member and communicate therewith, so that fluid may be injected into a patient's tissues at multiple locations via the needle elements.

Where the needle element is ejectably disposed in a hollow outer needle, the instrument further comprises at least one electrical conductor operatively connected to the needle element for transmitting a current through the needle element to heat the needle element to the activation temperature.

A medical method comprises, in accordance with the present invention, inserting an endoscope into a patient, moving an elongate needle through a biopsy channel of the endoscope, the needle having a length of greater than one centimeter and being flexible to negotiate bends in the biopsy channel, ejecting the needle from the biopsy channel, subsequently inserting the needle into internal tissues of the patient proximate to a distal end of the endoscope, and injecting fluid into the internal tissues via the inserted needle. The needle may have a memory for a nonlinear configuration and may assume that configuration upon ejection from the biopsy channel.

Pursuant to another aspect of the present invention, the method further comprises conducting electrical energy through the needle after moving of the needle through the biopsy channel, thereby heating the needle to a predetermined activation temperature at which the needle forms the nonlinear configuration.

In another embodiment the present invention, a method utilizes a medical instrument including at least one needle element made of an electrically resistant material, the needle being preformed to assume a desired use configuration upon attainment of a predetermined activation temperature above room temperature. The method includes inserting the needle into a patient, thereafter heating the needle to the activation temperature so that the needle assumes the desired use configuration, and subsequently manipulating the needle inside the patient to engage internal tissues with the needle in the desired use configuration. The inserting of the needle may include moving the needle though a biopsy channel of an endoscope inserted into the patient.

In a related embodiment of the present invention, a medical method utilizes a medical instrument including a plurality of needle elements all made of an electrically resistant material, the needle elements being preformed to assume respective desired use configurations upon attainment of a predetermined activation temperature above room temperature. The method includes inserting the needle elements substantially simultaneously through a tubular member into a patient, thereafter heating the needle elements to the activation temperature so that the needle elements assume the respective desired use configurations, moving the needle elements inside the patient to engage internal tissues with the needle elements, and using the needle elements in the respective desired use configurations to perform a procedure on the internal tissues. The inserting of the needles includes moving the needles through a biopsy channel of an endoscope inserted in the patient.

BRIEF DESCRIPTION OF THE DRAWINGS

FIG. 1 is a schematic perspective view of an endoscopic instrument assembly in accordance with the present invention.

FIG. 2 is a schematic perspective view, partially broken away, of a distal end portion of the instrument assembly of FIG. 1, showing the instrument assembly as deployed via a flexible insertion member of an endoscope.

DETAILED DESCRIPTION OF THE PREFERRED EMBODIMENTS

Figure 3:
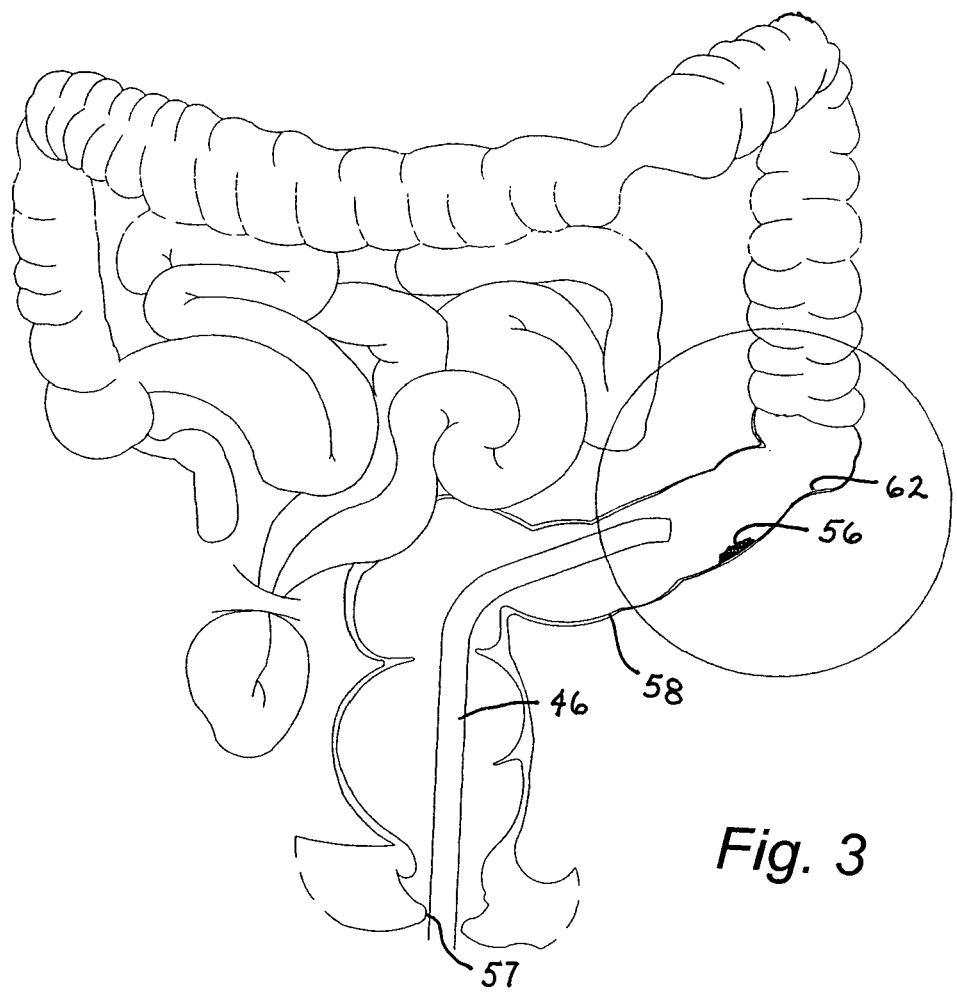
FIG. 3 is a diagram of a lower portion of a human digestive tract, showing the endoscope insertion member of FIG. 2 inserted into a colon shown in cross-section.

As illustrated in FIGS. 1 and 2, a medical instrument assembly for use in fluid injection procedures comprises a plurality of hollow needle elements 20 connected at their proximal ends to a distal end of a tubular member 22 in the form of a flexible hollow wire. Needle elements 20 communicate with a lumen (not shown) of tubular member 22 to enable a distribution of a diagnostic or therapeutic fluid into organic tissues of a patient at a plurality of spaced locations essentially simultaneously. Tubular member 22 is provided at a proximal end with a fluid introduction port 24 communicating with the lumen.

The instrument assembly of FIGS. 1 and 2 includes an actuator subassembly 26 including a cylindrical body portion 28 formed with a longitudinal slot 30 and carrying a slidably mounted shifter 32. Shifter 32 is provided with a pair of opposed flanges 34 and 36 having finger holes 38 and 40. Shifter 32 is connected to tubular member 22 for moving the tubular member alternately in the distal direction and the proximal direction through a flexible tubular sheath 42 that is fixed at a proximal end to cylindrical body portion 28. Sheath 42 has a sufficiently small diameter to enable insertion of the sheath, together with tubular member 22, into a biopsy channel 44 of an endoscope insertion member 46.

Cylindrical body portion 28 of actuator subassembly 26 is provided with a plurality of spring-loaded balls or beads 48 spaced from each other longitudinally along the body portion. Balls or beads 48 are alternatively engageable in an aperture or recess 50 in shifter 32 for temporarily locking the shifter to the actuator body portion in any one of a plurality of pre-established positions.

Needle elements 20 are made of a material with a memory such as superelastic Nitinol. Needle elements 20 have a predetermined rest configuration relative to one another. The application of an external force of a limited magnitude to the needle elements 20 can deform them out of the rest configuration into another configuration. Needle elements 20 reassume the rest configuration upon a cessation or termination of the external force.

As shown in FIGS. 1 and 2, the rest configuration of needles 20 is an expanded bulbous ovoid configuration in which the needle elements 20 extend away from the distal end of tubular member 22 and are each convex on an outer side facing away from the other needle elements and concave on an inner side. In this bulbous ovoid rest configuration, needle elements 20 have tips 52 that are angled inwardly at a distal tip of the medical instrument. Needle elements 20 may extend in an axially symmetric distribution about a longitudinal axis (not shown) of tubular member 22 at the distal end thereof. In addition, additional needle elements 53 (FIG. 2) having a straight configuration in the expanded state of the instrument may be provided. Needle elements 53, as well as needle elements 20, may have apertures only at their distal tips or may have multiple apertures spaced along their sidewalls, as discussed hereinbelow.

Figure 4A:
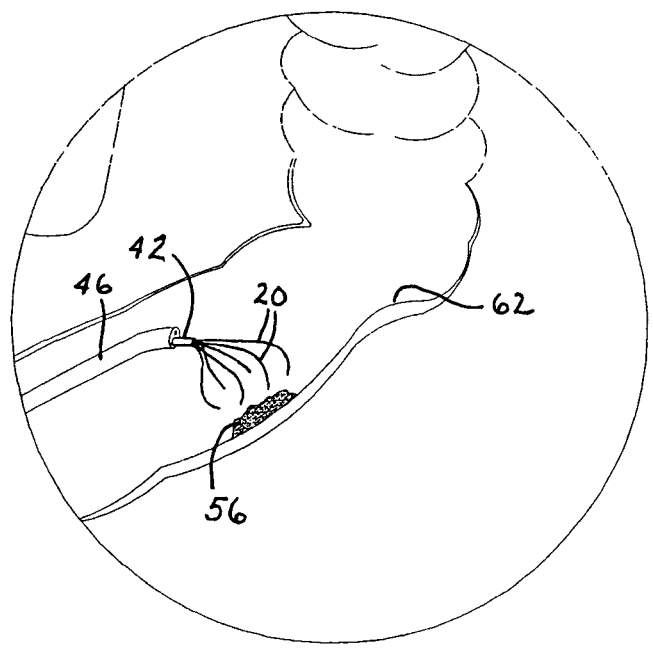
FIGS. 4A-4E are schematic partial cross-sectional views of the colon of FIG. 3 on a larger scale, showing successive steps in the utilization of the instrument assembly of FIGS. 1 and 2 to create an artificial pedicle under a sessile lesion.
Figure 4B:
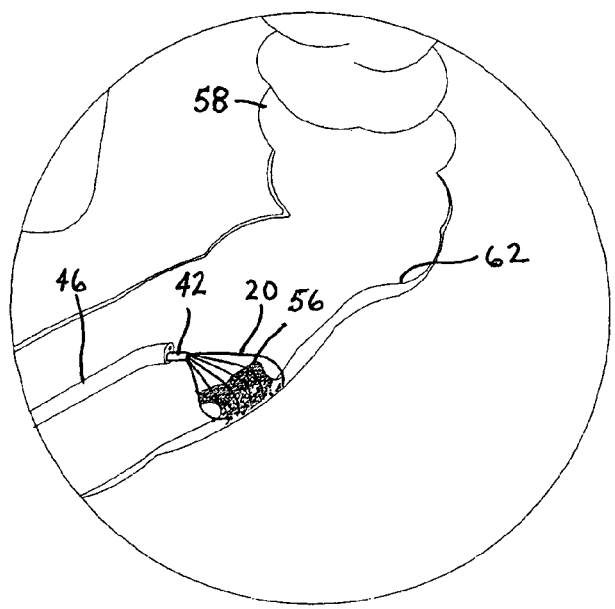

The rest configuration of needle elements 20 is designed to optimize the utilization of the instrument assembly of FIGS. 1 and 2 in the generation of an artificial pedicle 54 under a sessile lesion 56 (see FIGS. 4B-4E). As shown in FIG. 3, endoscope insertion member 46 is inserted through a patient's rectum 57 and into the colon 58. Insertion member 46 is provided with optical elements such as a lens 60 to enable visual inspection of an inner wall 62 of colon 58. When the visual inspection detects sessile lesion 56, sheath 42 with tubular member 22 and needle elements 20 disposed therein is inserted through biopsy channel 44 until a distal end portion of sheath 42 protrudes from the distal end of the biopsy channel, as shown in FIG. 4A. Shifter 32 is then moved in the distal direction to eject needle elements 20 from the distal end portion of sheath 42. Upon their ejection, needle elements 20 automatically assume the rest or unstressed configuration of FIGS. 1 and 2 under the action of internal spring forces of the Nitinol material. Subsequently, endoscope insertion member 46 and/or the instrument assembly of FIGS. 1 and 2 is manipulated to insert the tips 52 of needle elements 20 into the colon wall 62 in a substantially circular locus about the sessile lesion 56. Prior to this operation, a dye may be injected into the lesion to facilitate the identification of the boundaries of the lesion and the placement of needle tips 52 thereabout.

Figure 4C:
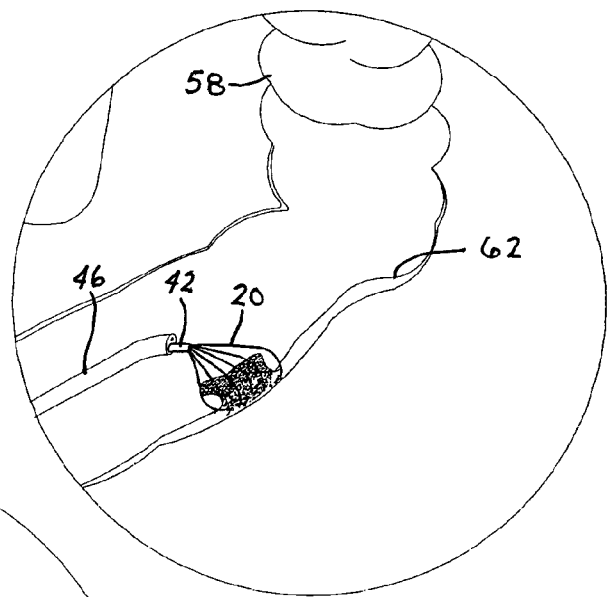
Figure 4D:
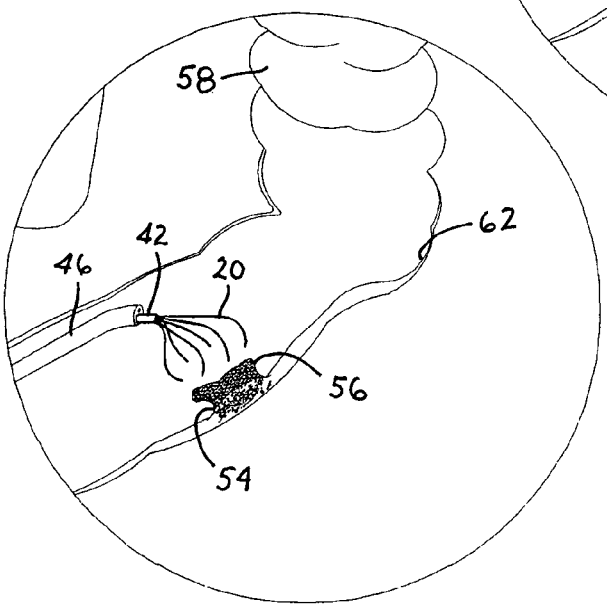

After the tips 52 of needle elements 20 are initially placed into contact with organic tissues of colon wall 62 about lesion 56 and inserted into the tissues (FIG. 4B), shifter 32 may be pushed in the distal direction to force needle tips 52 under the peripheral region of the lesion, as depicted in FIG. 4C. Upon the completed positioning of needle tips 52 in colon wall 62 at lesion 56, a saline solution or dye or other biocompatible liquid is injected into tubular member 22 via, for example, a hypodermic type syringe 64 attached to port 24 (FIG. 1). This fluid is distributed through needle elements 20 into the organic tissues of the colon wall 62 underlying lesion 56 to thereby expand the tissues to form pedicle 54 as shown in FIGS. 4B through 4E. Because of the structure of the injection instrument of FIGS. 1 and 2, the fluid is introduced into the organic tissues of colon wall 62 substantially simultaneously at a plurality of spaced points disposed in a circular locus. Thereafter tubular member 22 is manipulated to withdraw needle tips 52 from colon wall 62, as shown in FIG. 4D. Shifter 32 is pulled in a proximal direction to retract needle elements 20 back into the distal end portion of sheath 42, which is then extracted from biopsy channel 44. Subsequently, a cauterization snare assembly 66 (FIG. 4E) is deployed via biopsy channel 44. Snare assembly includes a cauterization loop 68 and an auxiliary loop 70 with a capture pouch 72. Loops 68 and 70 are placed over the raised lesion 56 and tightened about pedicle 54. Electrical current is then conducted through loop 68 to cut through pedicle 54 and release lesion 56 into pouch 72 for extraction from the patient.

Figure 5:
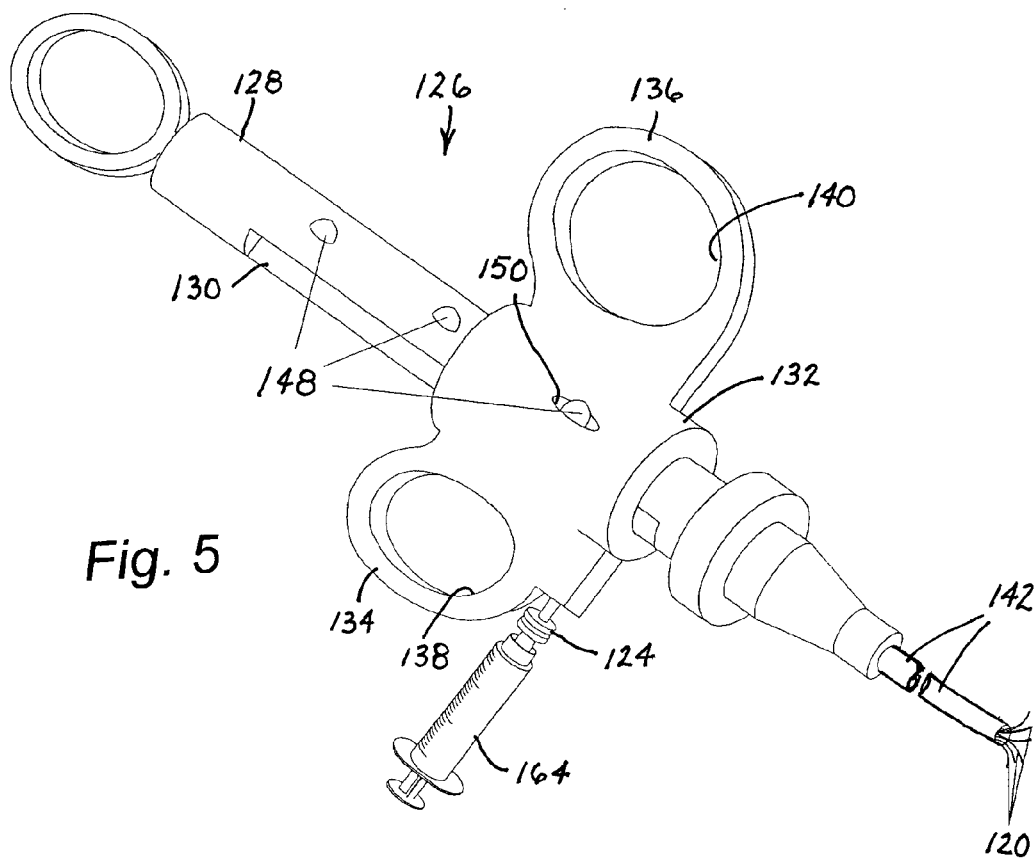
FIG. 5 is a schematic perspective view of another endoscopic instrument assembly in accordance with the present invention.
Figure 6:
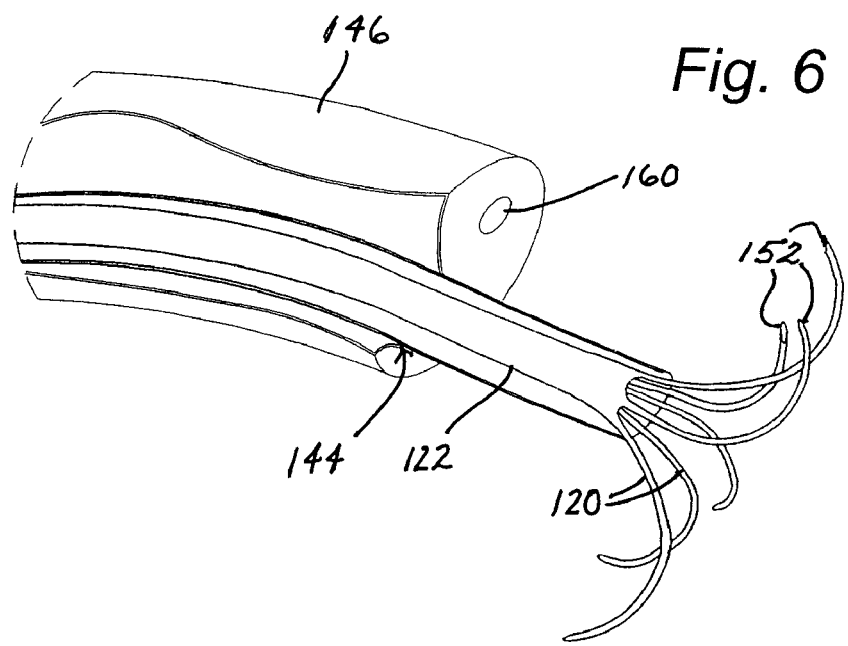
FIG. 6 is a schematic perspective view, partially broken away, of a distal end portion of the instrument assembly of FIG. 5, showing the instrument assembly as deployed via a flexible insertion member of an endoscope.

As illustrated in FIGS. 5 and 6, another medical instrument assembly for use in fluid injection procedures comprises a plurality of hollow needle elements 120 connected to a distal end of a tubular member 122 in the form of a flexible hollow wire. Needle elements 120 communicate with a lumen (not shown) of tubular member 122 to enable a distribution of a diagnostic or therapeutic fluid into organic tissues of a patient at a plurality of spaced locations essentially simultaneously. Tubular member 122 is provided at a proximal end with a fluid introduction port 124 communicating with the lumen.

The instrument assembly of FIGS. 5 and 6 includes an actuator subassembly 126 including a cylindrical body portion 128 formed with a longitudinal slot 130 and carrying a slidably mounted shifter 132. Shifter 132 is provided with a pair of opposed flanges 134 and 136 having finger holes 138 and 140. Shifter 132 is connected to tubular member 122 for moving the tubular member alternately in the distal direction and the proximal direction through a flexible tubular sheath 142 that is fixed at a proximal end to cylindrical body portion 128. Sheath 142 has a sufficiently small diameter to enable insertion of the sheath, together with tubular member 122, into a biopsy channel 144 of an endoscope insertion member 146.

Cylindrical body portion 128 of actuator subassembly 126 is provided with a plurality of spring-loaded balls or beads 148 spaced from each other longitudinally along the body portion. Balls or beads 148 are alternatively engageable in an aperture or recess 150 in shifter 132 for temporarily locking the shifter to the actuator body portion in any one of a plurality of pre-established positions.

Needle elements 120 are made of a material with a memory such as superelastic Nitinol. Needle elements 120 have a predetermined rest configuration relative to one another. The application of an external force of a limited magnitude to the needle elements 120 can deform them out of the rest configuration into another configuration. Needle elements 120 reassume the rest configuration upon a cessation or termination of the external force.

As shown in FIGS. 5 and 6, the rest configuration of needles 120 is a grappling hook configuration in which the needle elements 120 extend away from the distal end of tubular member 122 and are each concave on an outer side facing away from the other needle elements and convex on an inner side. In this grappling hook configuration, needle elements 120 have tips 152 that are angled outwardly and proximally at a distal tip of the medical instrument. Needle elements 120 may extend in an axially symmetric distribution about a longitudinal axis (not shown) of tubular member 122 at the distal end thereof.

Figure 7:
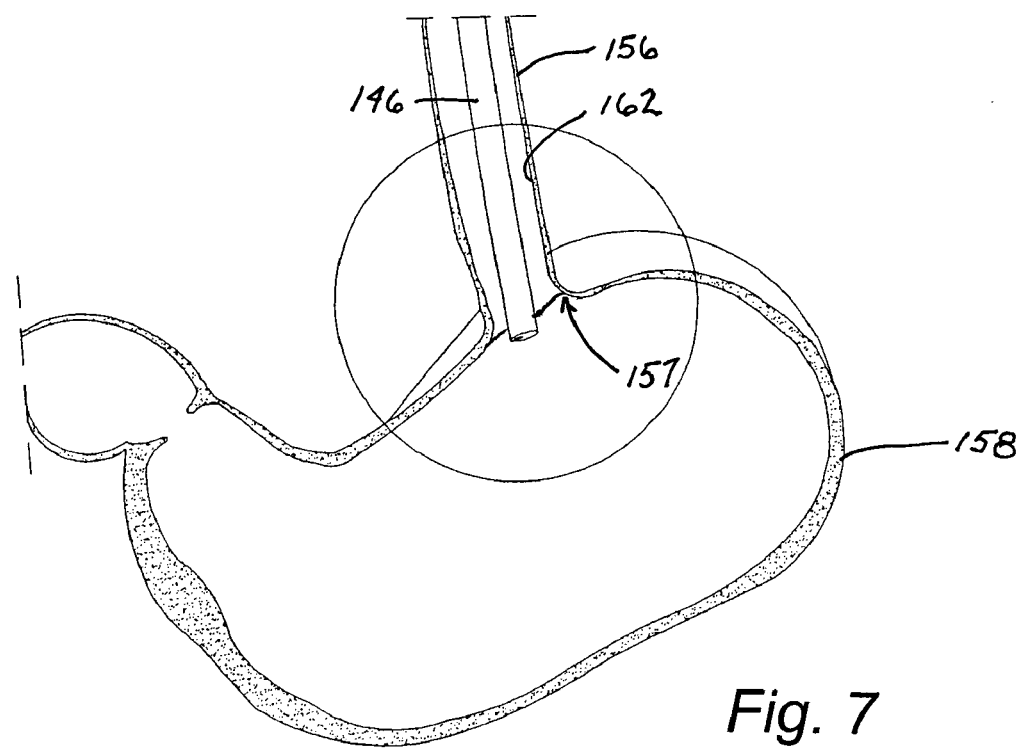
FIG. 7 is a cross-sectional view of an upper portion of a human digestive tract, showing a distal end portion of the endoscope insertion member of FIG. 6 inserted through an esophagus to a stomach.
Figure 8A:
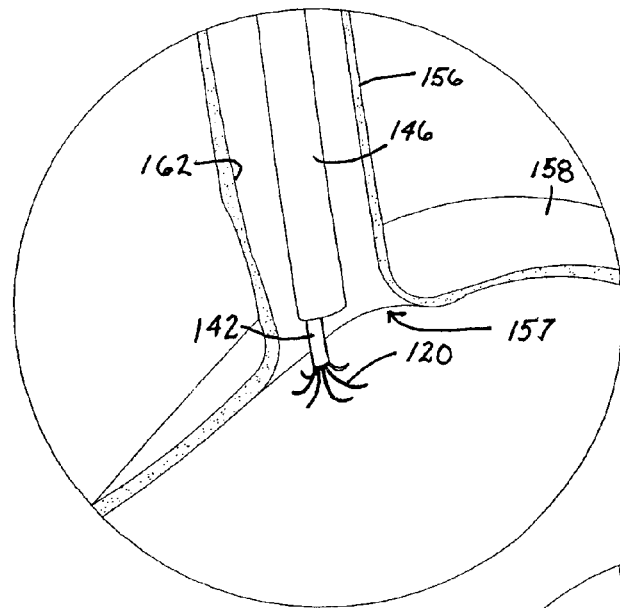
FIGS. 8A-8F are schematic partial cross-sectional views of the stomach of FIG. 7 on a larger scale, showing successive steps in the utilization of the instrument assembly of FIGS. 6 and 7 to create an artificial gastro-esophageal sphincter.
Figure 8B:
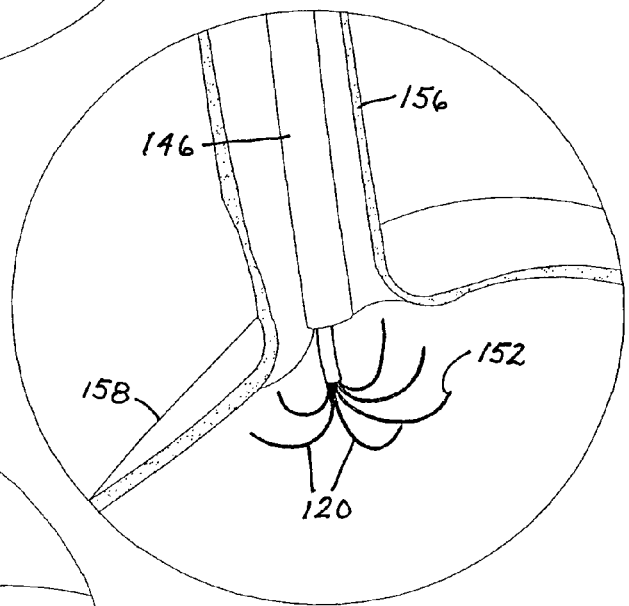
Figure 8C:
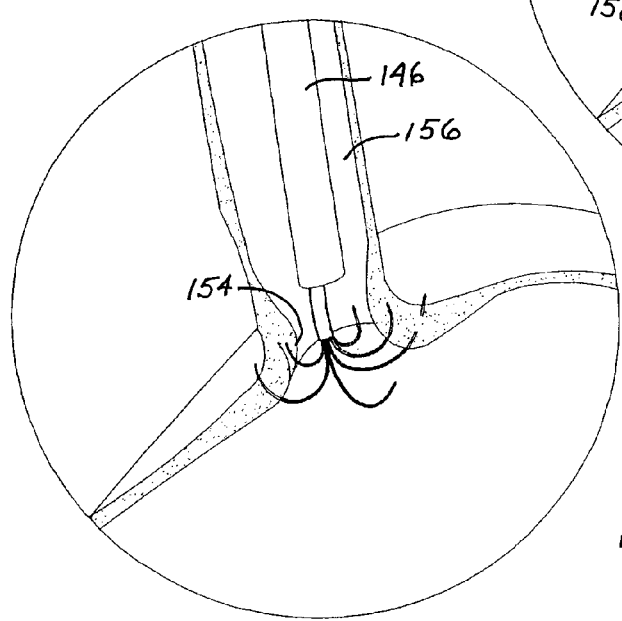
Figure 8D:
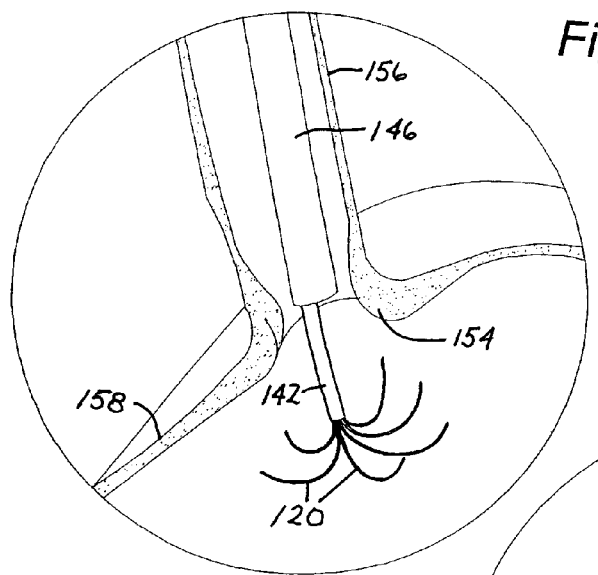
Figure 8E:
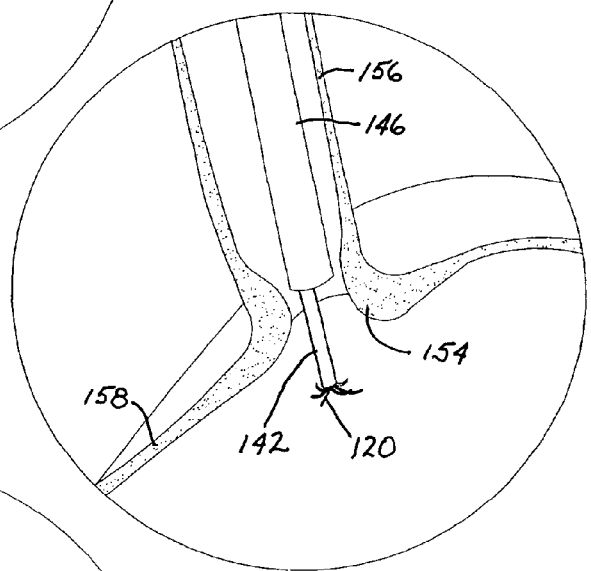
Figure 8F:
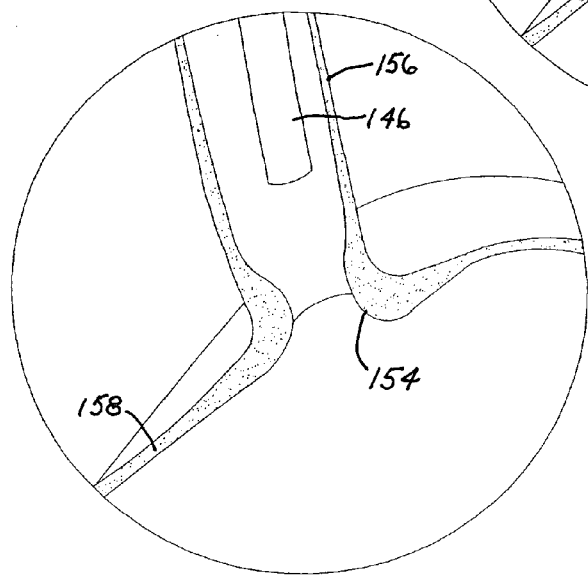

The rest configuration of needle elements 120 is designed to optimize the utilization of the instrument assembly of FIGS. 5 and 6 in the generation of an artificial gastro-esophageal sphincter 154 at a lower end of an esophagus 156 (see FIGS. 8D-8F). As shown in FIG. 7, endoscope insertion member 146 is inserted through esophagus 156 to a junction 157 of the esophagus with a stomach 158. Insertion member 146 is provided with optical elements such as a lens 160 to enable visual inspection of an inner wall 162 of esophagus 156. When the visual inspection detects the gastro-esophageal junction 157, sheath 142 with tubular member 122 and needle elements 120 disposed therein is inserted through biopsy channel 144 until a distal end portion of sheath 142 protrudes from the distal end of the biopsy channel, as shown in FIG. 8A. Shifter 132 is then moved in the distal direction to eject needle elements 120 from the distal end portion of sheath 142. FIG. 8A shows needles 120 in a partially ejected state, while FIG. 8B shows the needles in the fully expanded or opened grappling-hook configuration. Upon their ejection, needle elements 120 automatically assume the rest or unstressed configuration of FIGS. 5 and 6 under the action of internal spring forces of the Nitinol material. Subsequently, endoscope insertion member 146 and/or the instrument assembly of FIGS. 5 and 6 is manipulated to insert the tips 152 of needle elements 120 into gastro-esophageal junction 157 in a substantially circular locus about the junction.

Figure 4E:
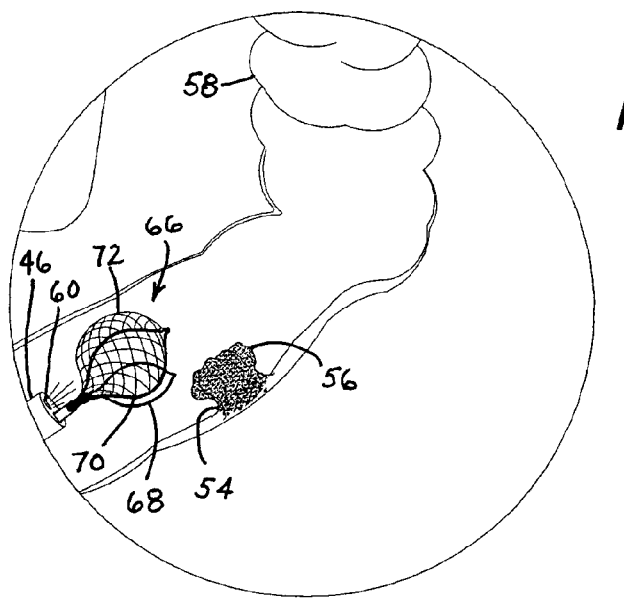

After the tips 152 of needle elements 120 are initially placed into contact with organic tissues of gastro-esophageal junction 157, shifter 132 may be pulled in the proximal direction to force needle tips 152 into the tissues, as depicted in FIG. 4C. Upon the completed positioning of needle tips 152 at gastro-esophageal junction 157, collagen, gel or other biocompatible fluidic material of long lasting character is injected into tubular member 122 via, for example, a hypodermic type syringe 164 attached to port 124 (FIG. 5). This fluid is distributed through needle elements 120 into the organic tissues of the gastro-esophageal junction 157 to thereby expand the tissues to form sphincter 154 as shown in FIGS. 8D-8F. Because of the structure of the injection instrument of FIGS. 5 and 6, the fluid is introduced into the gastro-esophageal tissues substantially simultaneously at a plurality of spaced points disposed in a circular locus along the esophageal lumen (not separately designated). Thereafter shifter 132 is pushed in the proximal direction to extract needle tips 152 from gastro-esophageal junction 157, as shown in FIG. 8D. Shifter 132 is then pulled in the proximal direction to retract needle elements 120 back into the distal end portion of sheath 142 (FIG. 4E). At that point, endoscope insertion member 146 is withdrawn upwardly through esophagus 156, with or without a prior retraction of sheath 142 into biopsy channel 144 (FIG. 4F).

Figure 9:
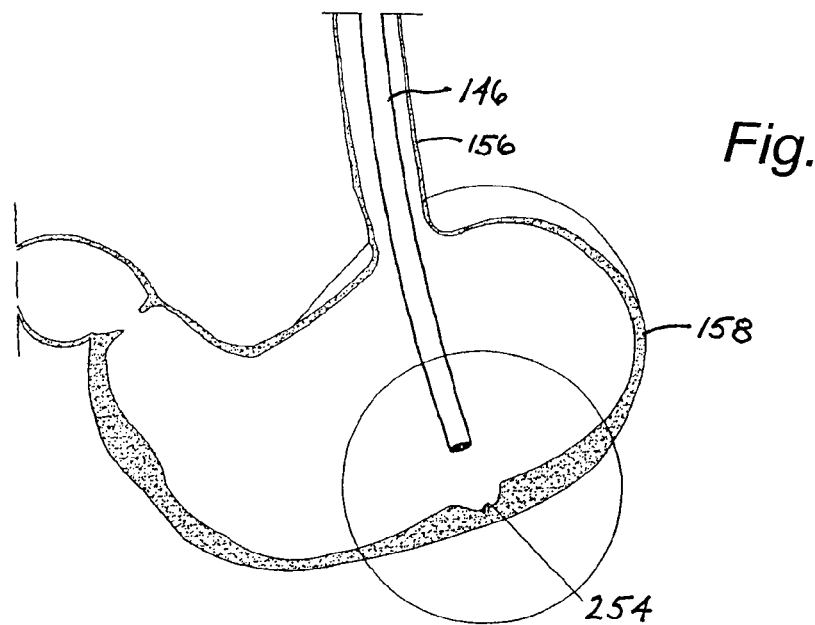
FIG. 9 is a cross-sectional view of an upper portion of a human digestive tract, showing a distal end portion of the endoscope insertion member of FIG. 6 inserted into a stomach.
Figure 10A:
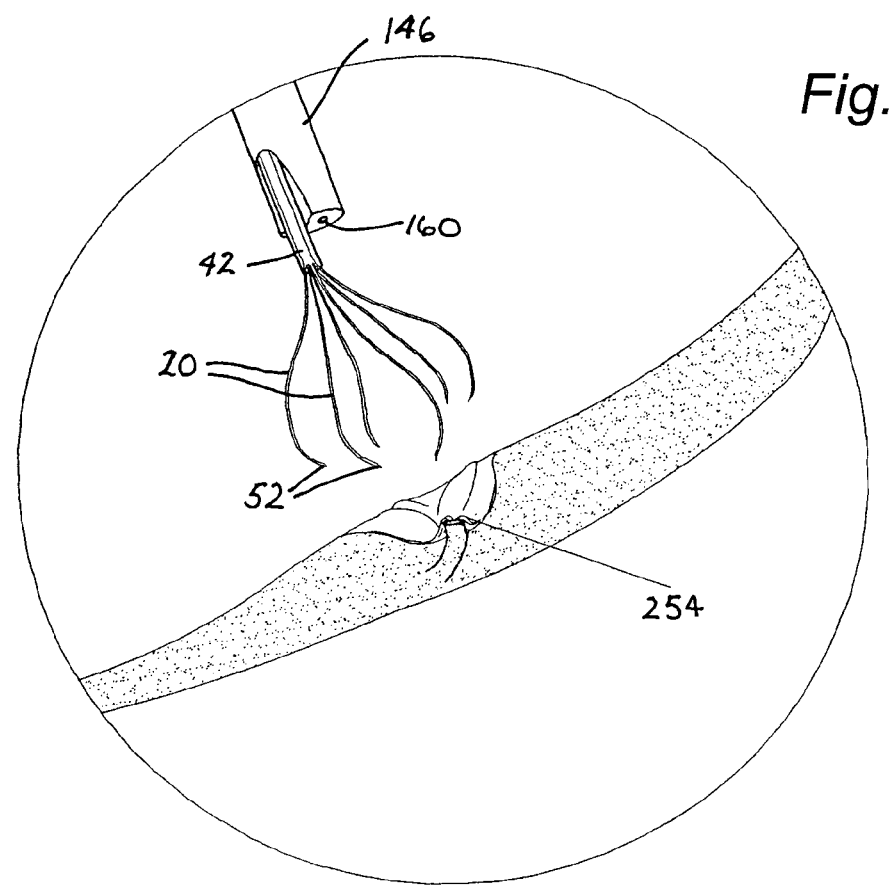
FIGS. 10A-10F are schematic partial cross-sectional views of the stomach of FIG. 9 on a larger scale, showing successive steps in the utilization of the instrument assembly of FIGS. 1 and 2 to create inject a coagulant, collagen, a sclerosing composition, or other blood-flow reducing agent into the stomach wall at the site of a bleeding ulcer.

The fluid injection instrument of FIGS. 1 and 2 may be used in other procedures, for instance, in the treatment of a bleeding ulcer 254 (FIG. 9). In this case, the dimensions of sheath 42, tubular member 22 and needle elements 20 are selected to enable insertion through biopsy channel 144 of endoscope insertion member 146. The bulbous or ovoid rest configuration of needle elements 20 is suitable for injection of a coagulant, collagen, a sclerosing composition, or other blood-flow-reducing agent into tissues of a stomach wall 256 at multiple locations about ulcer 254 (see FIGS. 10A-10C). As shown in FIG. 9, endoscope insertion member 146 is inserted through a patient's esophagus 257 and into the stomach 258. The optical elements of insertion member 146 are used to visually inspect stomach wall 256. Upon a detection of ulcer 254, sheath 42 with tubular member 22 and needle elements 20 disposed therein is inserted through biopsy channel 144 until a distal end portion of sheath 42 protrudes from the distal end of the biopsy channel, as shown in FIG. 10A. Shifter 32 is then moved in the distal direction to eject needle elements 20 from the distal end portion of sheath 42. Upon their ejection, needle elements 20 automatically assume the rest or unstressed configuration of FIGS. 1 and 2 (see FIG. 10A) under the action of internal spring forces of the Nitinol material. Subsequently, endoscope insertion member 146 and/or the instrument assembly of FIGS. 1 and 2 is manipulated to insert the tips 52 of needle elements 20 into stomach wall 256 in a substantially circular locus about the ulcer 254.

Figure 10B:
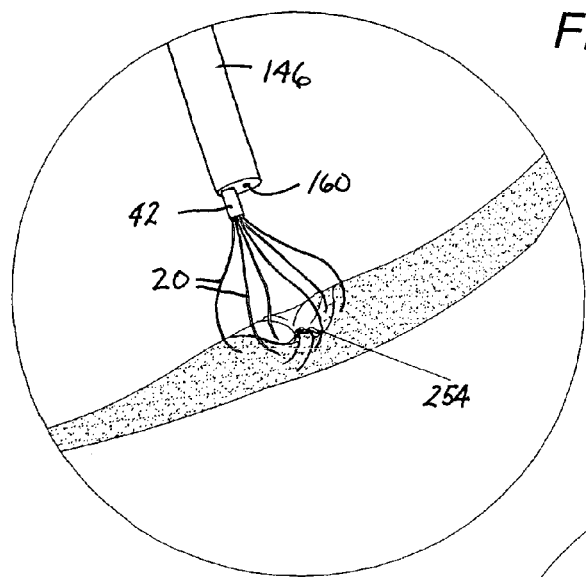
Figure 10C:
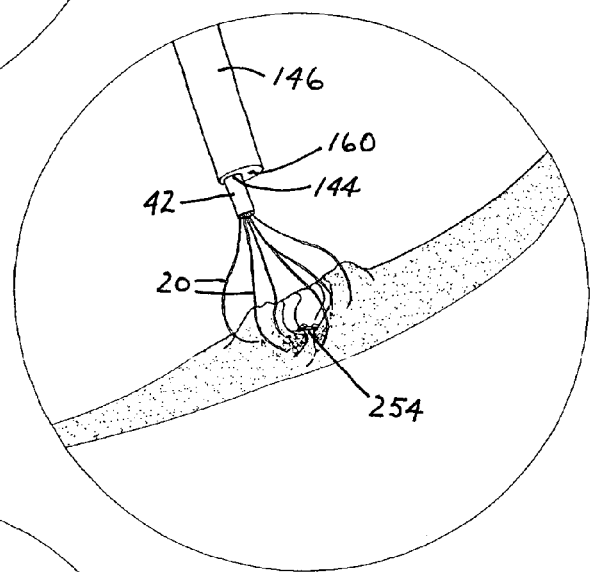
Figure 10D:
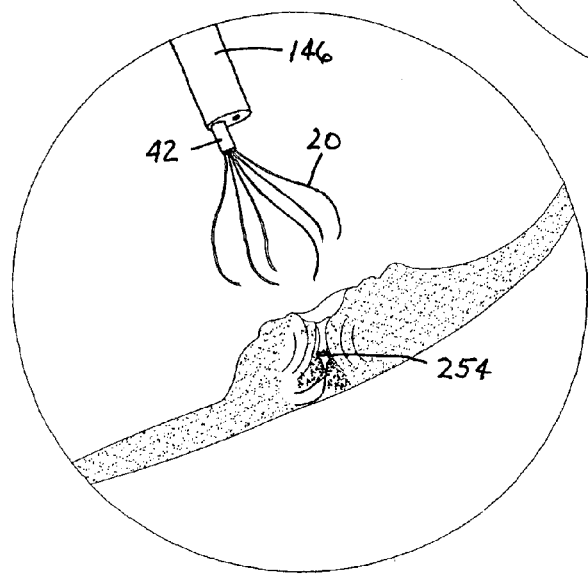
Figure 10E:
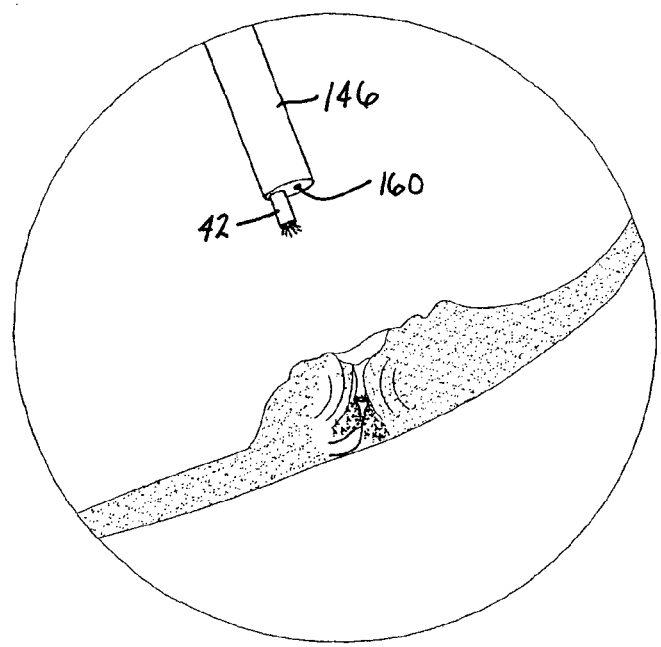
Figure 10F:
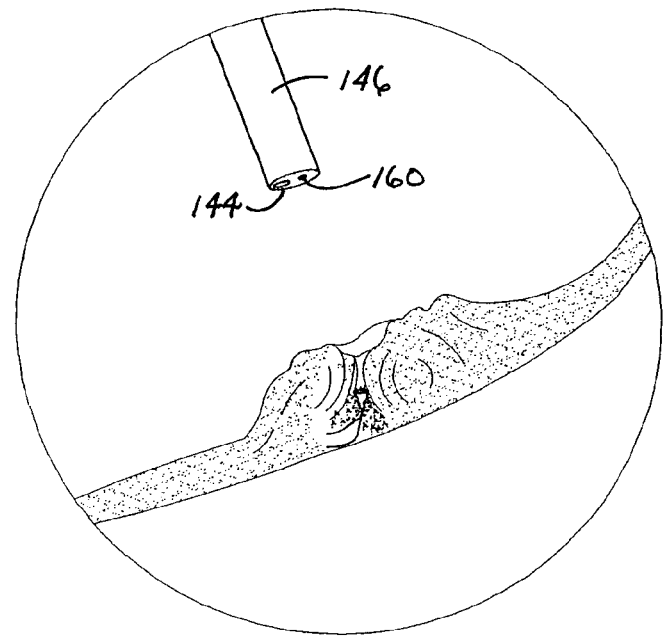

After the tips 52 of needle elements 20 are initially placed into contact with stomach wall 256 about ulcer 254, shifter 32 may be pushed in the distal direction to force needle tips 52 into the gastric tissues about the ulcer 254, as depicted in FIG. 10B. An appropriate bead or ball 48 (FIG. 1) is received in recess 50 to lock shifter 32 with needle elements 20 in the expanded use configuration of FIGS. 1 and 2. Upon the completed positioning of needle tips 52 in stomach wall 256 at ulcer 254, a coagulant, collagen, or other blood-flow-reducing composition is injected into tubular member 22 via syringe 64 (FIG. 1). This composition is distributed through needle elements 20 into the organic tissues of the stomach wall 256 under and around ulcer 254 to form clots in the blood vessels supplying the ulcer. Because of the structure of the injection instrument of FIGS. 1 and 2, the blood-flow-reducing composition is introduced into the organic tissues of stomach wall 256 substantially simultaneously at a plurality of spaced points disposed in a circular locus. Thereafter tubular member 22 is manipulated to withdraw needle tips 52 from stomach wall 256, as shown in FIG. 10D. Shifter 32 is pulled in a proximal direction to retract needle elements 20 back into the distal end portion of sheath 42, as shown in FIG. 10E. Sheath 42 is then extracted from biopsy channel 44 (FIG. 10F) and endoscope insertion member 146 is removed from the patient.

Figure 11:
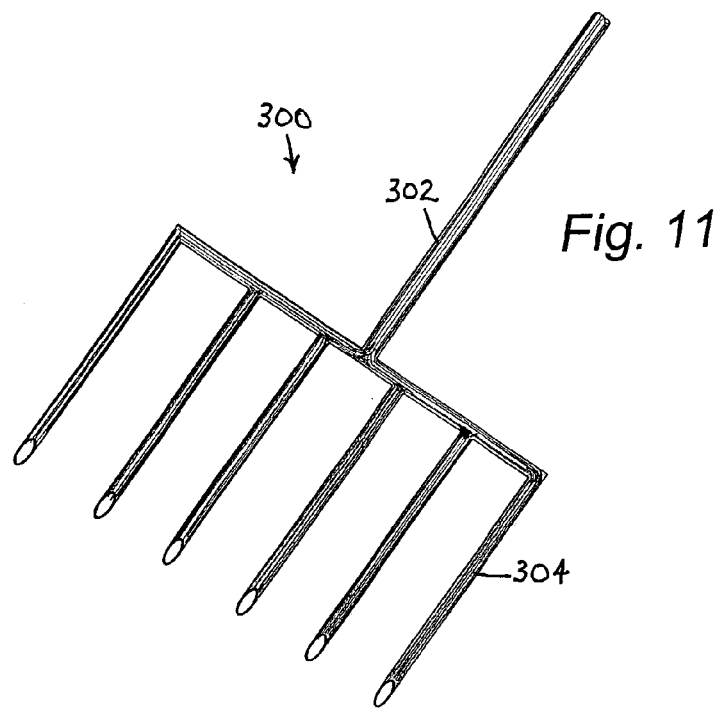
FIG. 11 is a schematic elevational view of a distal end portion of a medical instrument, in accordance with the present invention, for injecting a fluid into organic tissues of a patient at a plurality of spaced locations simultaneously.

FIG. 11 depicts a medical instrument 300 for injecting a fluid into organic tissues of a patient at a plurality of spaced locations simultaneously. Instrument 300 includes a tubular member 302 connected at a distal end to a plurality of needle elements 304 extending parallel to one another in a planar configuration similar to a fork. Tubular member 302 and needle elements 304 may be made of a rigid material such as stainless steel or a titanium alloy and are useful, for instance, in injecting an anesthetic, antibacterial and/or coagulant composition into skin tissues along a linear wound such as a cut. Such an instrument is particularly effective for emergency room procedures.

Figure 12:
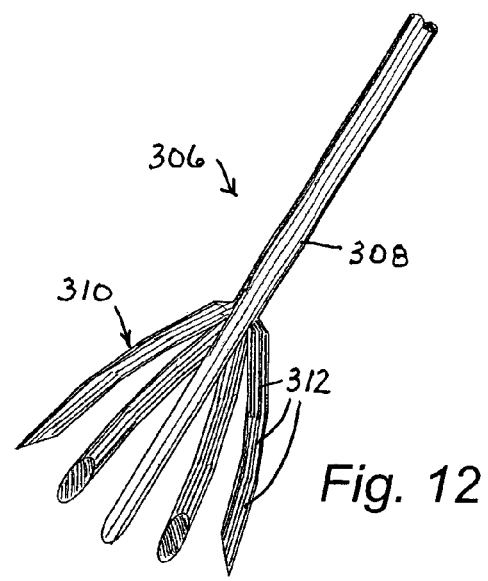
FIG. 12 is a schematic elevational view of a distal end portion of a further medical instrument, in accordance with the present invention, for injecting a fluid into organic tissues of a patient at a plurality of spaced locations simultaneously.

FIG. 12 shows another medical instrument 306 for injecting a fluid into organic tissues of a patient at a plurality of spaced locations simultaneously. Instrument 306 includes a tubular member 308 connected at a distal end to a plurality of needle elements 310 each comprising a plurality of hollow linear segments 312. Segments 312 are each oriented at an angle to at least one adjacent segment of the same needle element 310. Needle elements 310 may extend in a planar configuration. Tubular member 302 and needle elements 304 may be rigid or flexible. In the latter case, the needle elements 310 may be made at least partially of a memory material such as superelastic Nitinol. Like instrument 300, instrument 306 may be used to inject an anesthetic, antibacterial and/or coagulant composition into skin tissues along a linear wound such as a cut.

Figure 13:
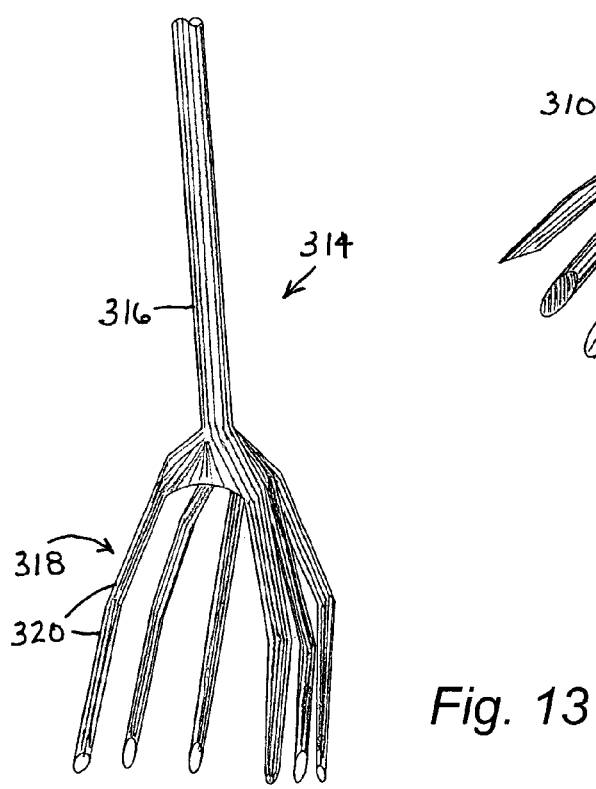
FIG. 13 is a schematic elevational view of a distal end portion of yet another medical instrument, in accordance with the present invention, for injecting a fluid into organic tissues of a patient at a plurality of spaced locations simultaneously.

FIG. 13 illustrates yet another medical instrument 314 for injecting a fluid into organic tissues of a patient at a plurality of spaced locations simultaneously. Instrument 314 includes a tubular member 316 connected at a distal end to a plurality of needle elements 318 each comprising a plurality of hollow linear segments 320. Segments 320 are each oriented at an angle to at least one adjacent segment of the same needle element 318. Needle elements 318 extend in a cup-shaped configuration and may be rigid or flexible. In the former case, needle elements 318 are made of a substance such as stainless steel or a titanium alloy and may be used to apply an anesthetic, antibacterial and/or coagulant composition into skin tissues along a two dimensional wound such as an abrasion or burn. In the latter case, the needle elements 318 may be made at least partially of a memory material such as superelastic Nitinol and may be used in an endoscopic, laparoscopic, arthroscopic, thoracoscopic, etc., operation.

Figure 14:
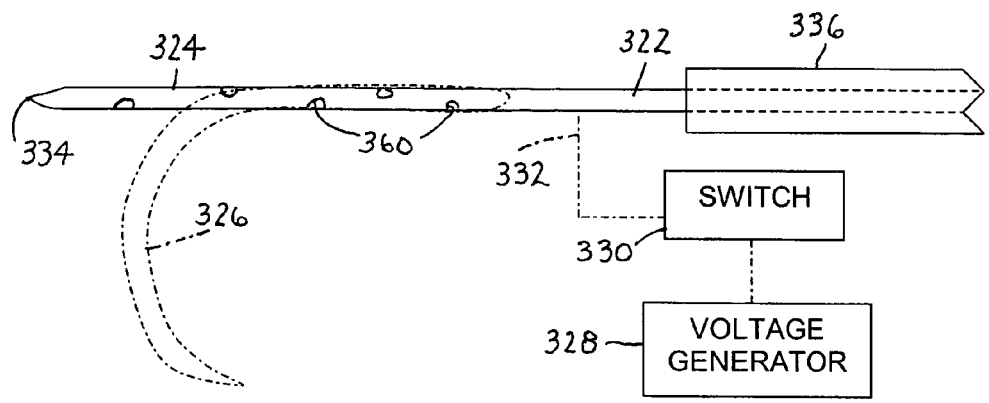
FIG. 14 is partially a schematic side elevational view and partially a block diagram of a further medical instrument in accordance with the present invention.

As depicted in FIG. 14, a medical injection instrument includes a tubular member 322 having a hollow distal end portion 324 in the form of a needle element made of a memory material such as shape memory Nitinol that is straight and flexible at room temperature and body temperature but assumes a desired arcuate configuration 326 when at a temperature above a pre-established activation or threshold temperature. That activation or threshold temperature is preferably above any temperature that the needle element 324 might attain prior to arrival at a destination or utilization site. Specifically, the activation or threshold temperature must be higher than sterilization temperatures and higher than any temperatures existing along the transit route of the needle element 324 to its destination.

Needle element 324 is at least a centimeter in length for suturing or injection into esophageal varices in a sclerotherapeutic procedure. At lower temperatures, needle element 324 is flexible enough to negotiate a biopsy channel of an endoscope disposed in a convoluted configuration inside a patient. Generating an electrical current in the needle element 324 controllably attains the activation temperature. To that end, a voltage or current generator 328 is connected to needle element 324 via a switch 330. The shape memory Nitinol has a resistance to electrical current flow that elevates the temperature of the Nitinol. Upon attainment of the activation temperature, the needle element 324 assumes the arcuate configuration determined at the time of manufacture.

Voltage generator 328 and switch 300 may be connected to needle element 324 via wires or other conductors 332 extending longitudinally along tubular member 322. In a monopolar-type circuit design, conductors 332 are connected to the needle element 324 at only one end thereof. In that case, a sharp tip 334 of the needle element 324 is inserted into the tissues of the patient so that current may be transmitted through those tissues, thereby completing the circuit through the needle element 324.

In a bipolar-type circuit design, electrical current is applied to needle element 324 prior to the injection thereof into the patient's tissues. In that case, an ancillary outer tubular element 336 in which needle element 324 and tubular member 322 are held is provided with conductors (not shown) that contact needle element 324 for circuit closure purposes. Electrical current is transmitted through needle element 324 from conductors 332 of tubular member 322 to the conductor in ancillary outer tubular element 336. Alternatively, all current may be conducted solely through outer tubular element (catheter) 336. In any case, current may be transmitted between needle element 324 and the conductors of tubular element 336 via a collar or a brush-type contact (not illustrated). Needle element 324 starts assuming its memory configuration 326 immediately upon release from ancillary outer tubular element 336.

It is to be noted that the needle elements of any of the instruments described herein may be heat activated to assume a desired configuration as discussed above with reference to FIG. 14.

Figure 15:
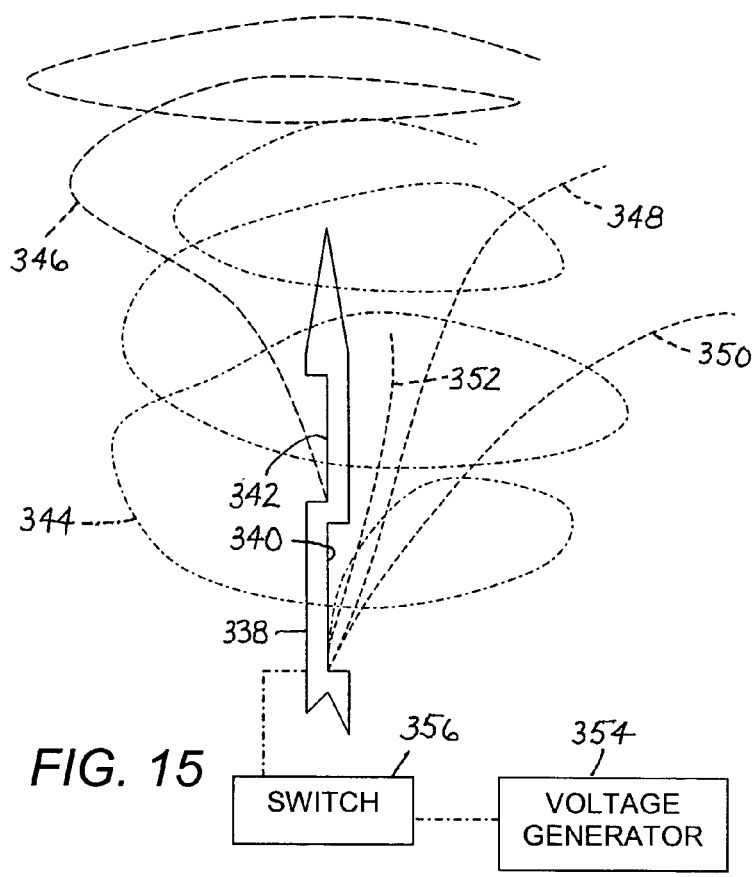
FIG. 15 is partially a schematic side elevational view and partially a block diagram of an additional medical instrument in accordance with the present invention.

FIG. 15 depicts a needle assembly for delivering a liquid such as a chemotherapeutic agent to tissues throughout a volume such as a tumor. A delivery needle 338 is provided with one or more openings 340, 342 for the ejection of a plurality of needles along respective paths 344, 346, 348, 350, 352 determined in part by predetermined memory configurations of the respective needles. The memory configurations may be assumed automatically by the needles at body temperature or may be assumed only upon attainment of a higher activation temperature. In the latter case, a voltage generator or current source 354 and switch(es) 356 are connected to the needle elements as discussed above with reference to FIG. 14. The activation temperature is preferably above any temperature that the needles might attain prior to arrival at a destination location inside a patient. Specifically, the activation temperature must be higher than sterilization temperatures and higher than any temperatures existing along the transit route of the needles to their destination.

The needles (not separately designated) introduced along paths 344, 346, 348, 350, 352 in a target tissue mass such as a tumor may have various shapes such as spiral (344, 346) or gently arced (348, 350) or even substantially straight (352) and various lengths. The needles (344, 346, 348, 350, 352) are preferably provided along their lengths with spaced apertures or holes 360 (FIG. 14) for enabling the delivery of fluid throughout the target tissue mass.

Figure 16:
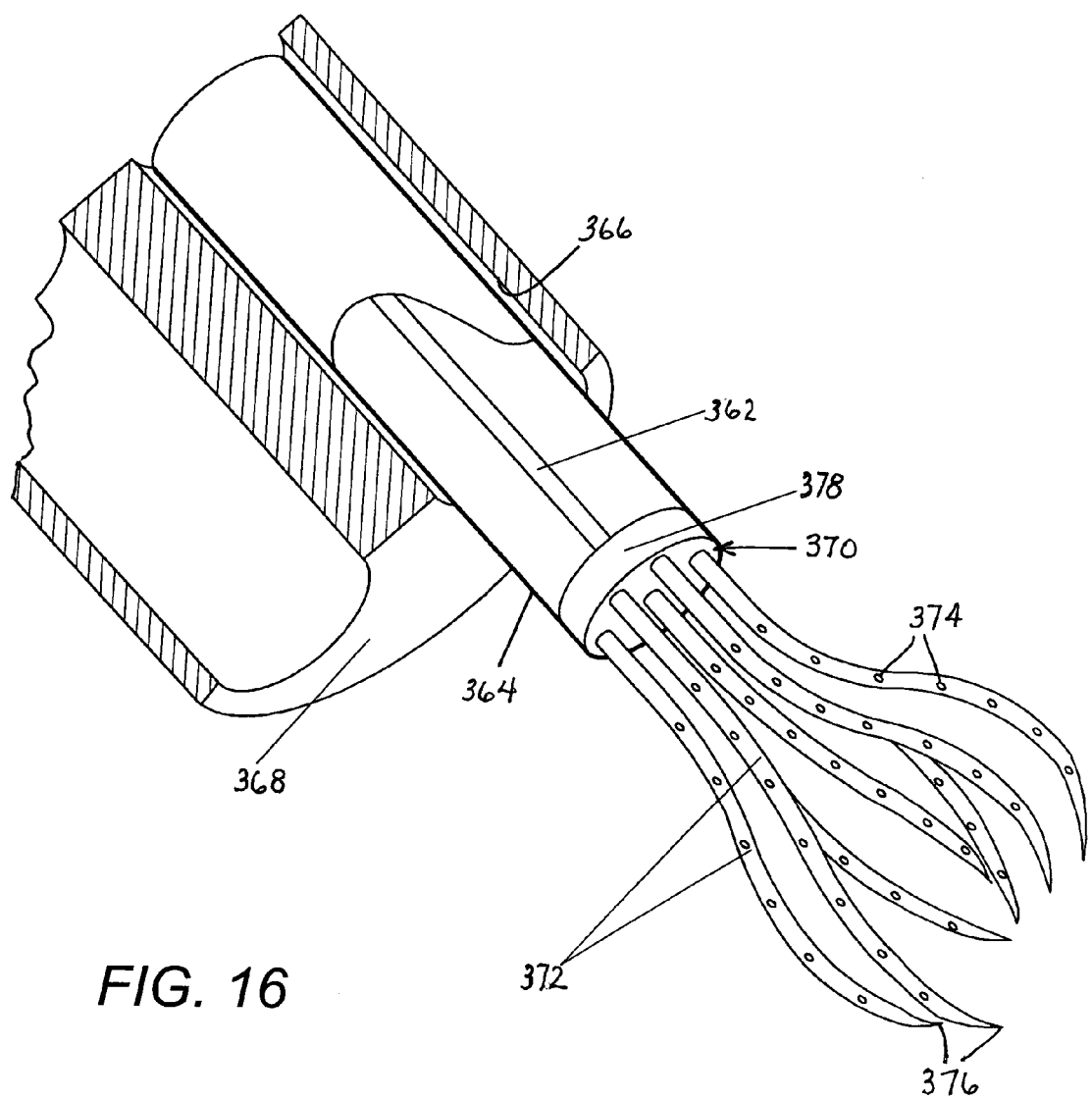
FIG. 16 is a schematic perspective or isometric view, partially broken away, of another medical instrument in accordance with the present invention.

FIG. 16 depicts another needle assembly for delivering a liquid such as a chemotherapeutic agent to tissues throughout a volume such as a tumor. An inner tubular member 362 extends longitudinally through and coaxially with an outer tubular member 364 in turn insertable through a biopsy channel 366 of an endoscopic insertion shaft 368. The inner tubular member 362 is connected at a distal end to a rigid cylindrical manifold 370 carrying on a distal side, a plurality of Nitinol needles 372 that assume predetermined partially arcuate configurations upon ejection from outer tubular member 364 into internal organic tissues of a patient. Needles 372 assume their arcuate configurations automatically upon ejection from tubular member 364. Needles 372 may be manufactured with a "shape memory" that may be activated at body temperature or at a higher temperature induced by the conduction of an electrical current through the needles (bipolar conduction). Preferably, the activation temperature is substantially higher than body temperature and greater than sterilization temperatures and than any temperatures existing along the transit route of the needles 372 to their destination.

Tubular member may be provided with a heating element separately from needles 372. The heating element exemplarily takes the form of a collar or ring disposed inside tubular member 364 at the distal end thereof. Needles 372 are in contact with the heating element prior to ejection of the needles from tubular member 364, whereby heat is transferred from the heating element to the needles. The heating element is made of an electrically resistive material. Electrical current may be delivered to the heating element via conductive wires or may be induced in the heating element, e.g., via an externally generated alternating magnetic field.

Inner tubular member 362 functions in part as a pusher element for enabling a user to eject needles 372 from outer tubular member 364, preferably after a distal end portion of the outer tubular member has been pushed out of biopsy channel 366. Inner tubular member 362 also serves as a conduit for the delivery of a desired fluid, such as a chemotherapeutic agent, to needles 372 via manifold 370. Needles 362 are preferably provided along their lengths with mutually spaced apertures or holes 374 for enabling the delivery of fluid throughout the target tissue mass.

Outer tubular member 364 functions in part to contain needles 372 during negotiation of biopsy channel 366 by an endoscopic instrument comprising tubular members 362 and 364, manifold 370, and needles 372. Outer tubular member 362 thus protects the biopsy channel 366 from inadvertent damage arising from instrument deployment. Outer tubular member 364 also ensures that the needles retain their sharp tips 376. Generally, tips 376 are solid, that is, devoid of apertures for the injection of fluid.

In a modified version of the embodiment of FIG. 16, manifold 370 may be rigidly attached about its cylindrical outer surface 378 to an inner surface (not designated) of outer tubular member 364. In that case, the proximal side of manifold 370 is perforated to enable communication between the lumen of outer tubular member 364 and manifold 370. Inner tubular member 362 may be formed as a solid rod in that event and functions solely as a pusher. In this modification, a third tubular member (not illustrated) may slidably surround outer tubular member 364 and house needles 372 during an instrument deployment operation.

Figure 17:
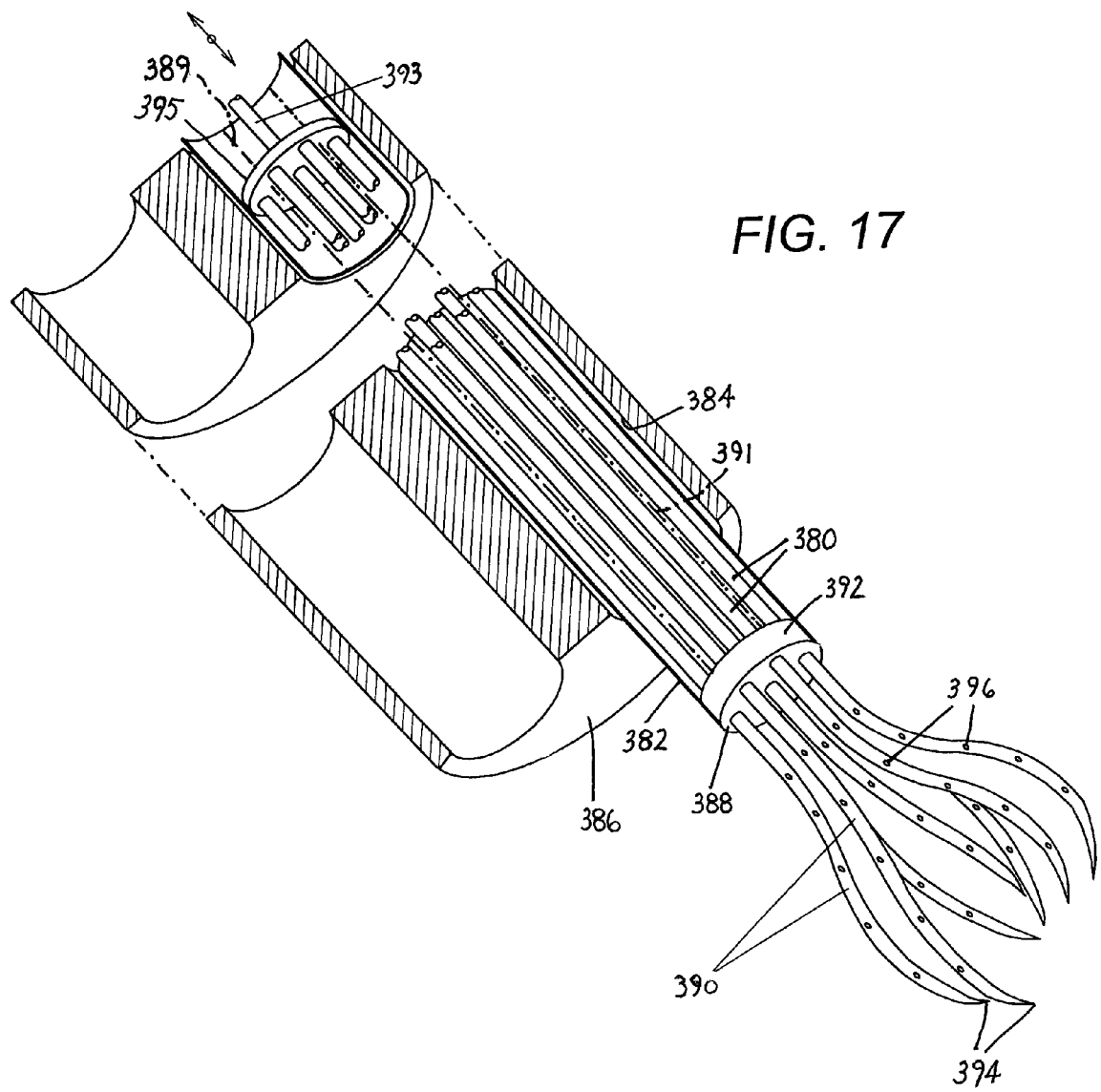
FIG. 17 is a schematic perspective or isometric view, partially broken away, of yet another medical instrument in accordance with the present invention.

As illustrated in FIG. 17, yet another needle assembly for delivering a liquid such as a chemotherapeutic agent to tissues throughout a volume such as a tumor includes an plurality of inner tubular members 380 extending longitudinally through a hollow elongate member or outer tubular member 382 in turn insertable through a biopsy channel 384 of an endoscopic insertion shaft 386. Proximate to their distal ends, inner tubular members 380 slidably traverse a cylindrical guide member 388 and terminate in respective Nitinol needles 390 that assume predetermined partially arcuate configurations upon ejection of the needles from biopsy channel 384 into internal organic tissues of a patient. Needles 390 assume their arcuate configurations automatically upon injection into the internal tissue of the patient. Needles 390 have a built-in spring bias or "memory" that forms the needles into the arcuate configurations shown in FIG. 17. The arcuate configurations may be independent of commonly encountered temperatures (e.g., room temperature or body temperature)(superelastic Nitinol) or may be dependent on temperature (shape memory Nitinol). In the latter case, the arcuate needle configurations are assumed only upon the attainment of a predetermined temperature such as body temperature or greater. Preferably, the activation temperature for the Nitinol needles 390 is higher than sterilization temperatures. To enable the generation of a higher-than-body temperature in needles 390, tubular members 380 may be made of an electrically conductive material for supplying the needles with electrical current. Alternatively, cylindrical guide member 388 may function in part as a heating element for increasing the temperatures of the needles 388. To that end, guide or collar 388 is coupled to a pair of wires 389 and 391 that supply a current to the guide or collar for heating purposes.

Cylindrical guide member 388 is bonded along its lateral outer surface 392 to an inner surface (not designated) of outer tubular member 382. Optionally, a third tubular member may be provided that surrounds outer tubular member 382 and needles 390 during an insertion of the needle instrument through biopsy channel 384. Alternatively, to avoid a potentially damaging contact between the sharp tips 394 of needles 390 and the wall (not separately designated) of biopsy channel 384, tubular members 380 may be initially disposed is a retracted position so that needle tips 394 barely protrude from cylindrical guide of collar 388.

Tubular members 380 function in part as pusher elements for enabling a user to eject needles 390 from outer tubular member 382, preferably after a distal end portion of the outer tubular member has been pushed out of biopsy channel 384. In the embodiment of FIG. 17, needles 390 are ejectable in unison, tubular members 380 being connected to a main inner tubular member 393 via a manifold element 395. Alternatively, tubular members 380 may be independently movable so that needle elements 390 are independently ejectable.

Inner tubular members 390 also serve as conduits for the delivery of a desired fluid, such as a chemotherapeutic agent, to needles 390. Needles 390 are preferably provided along their lengths with mutually spaced apertures or holes 396 for enabling the delivery of fluid throughout the target tissue mass.

Outer tubular member 382 functions in part to contain and restrict the lateral motion of inner tubular members 380. Needles 390 are slidably connected to the distal end of outer tubular member 382 via guide or collar 388.

The embodiments of FIGS. 16 and 17 may be additionally modified to have a plurality of needle elements extending from manifold 370 or 388 in multiple concentric circular arrays. These needle elements may have different shapes, for example, some straight and some arcuate, as discussed hereinabove with reference to needle elements 53 in FIG. 2.

The principles disclosed herein may be used in a medical therapeutic method wherein a hollow needle having a plurality of apertures spaced from one another longitudinally along the needle is inserted into tissues along and substantially parallel to a vascular lumen. Thereafter a fluid is injected substantially simultaneously from apertures into the tissues. The needle is preferably made of a memory material manufactured to have a first configuration at room temperature and to assume a second configuration upon attaining a predetermined activation temperature higher than room temperature. Such a needle may be made of an electrically resistant material so that conduction of current through the needle element elevates the temperature thereof. The needle may be inserted into the vascular wall of a blood vessel with the lumen and/into or internal body tissues adjacent to that blood vessel.

A hollow needle having a plurality of apertures spaced from one another longitudinally along the needle may be inserted into subcutaneous tissues along and substantially parallel to a skin surface. Thereafter a fluid is injected substantially simultaneously from apertures into the tissues. The fluid may be a collagen composition, an anesthesia composition, or a chemotherapeutic composition.

In a surgical method pursuant to the present disclosure, a needle device with multiple fluid ejection apertures is inserted into a polyp so that the apertures are distributed through at least a substantial portion of the polyp. A marker fluid such as a dye is injected substantially simultaneously through the apertures to mark the polyp.

Although the invention has been described in terms of particular embodiments and applications, one of ordinary skill in the art, in light of this teaching, can generate additional embodiments and modifications without departing from the spirit of or exceeding the scope of the claimed invention. For instance, the heating of needles or other surgical tools for purposes of effectuating a conformational change may be effectuated through the application of an alternating magnetic field. Such a field is generated externally to a patient, with the magnetic field lines extending into the patient with the result that an electrical current is induced in the needles or other tools.

Accordingly, it is to be understood that the drawings and descriptions herein are proffered by way of example to facilitate comprehension of the invention and should not be construed to limit the scope thereof.

What is claimed is:

1. An endoscopic medical instrument comprising an elongate tubular member containing a lumen extending from a proximal end to a distal end and a plurality of hollow needle elements connected to one end of said elongate member so that each of said hollow needle elements communicates at a proximal end with said lumen of said elongate tubular member, said elongate tubular member being sufficiently flexible, long and narrow to traverse a biopsy channel of a flexible fiberoptic endoscope, said needle elements extending in a direction away from said one end of said elongate tubular member, said needle elements each being convex on an outer side facing away from others of said needle elements and concave on an inner side facing said others of said needle elements so that said needle elements together define a bulbous ovoid shape, with tips of said needle elements angled inwardly at a distal tip of the medical instrument, said needle elements each being sufficiently flexible to negotiate bends in said biopsy channel, each of said hollow needle elements being provided with at least one aperture so that fluid may be delivered through said elongate tubular member into said hollow needle elements and out through the apertures in said hollow needle elements.

2. The medical instrument defined in claim 1 wherein said needle elements are at least partially made of resilient material with a memory so that said needle elements are alternately disposable in (a) a collapsed storage configuration inside said elongate member and (b) said bulbous ovoid shape.

3. The medical instrument defined in claim 2 wherein said needle elements are disposable in said storage configuration by the application of an external force, said needle elements having an internal spring bias tending to restore said needle elements to said bulbous ovoid shape.

4. The medical instrument defined in claim 1, further comprising at least one straight or linear hollow needle element connected to said elongate member proximate to said one end thereof, said at least one straight or hollow linear needle element being provided with at least one aperture.

* * * * *

UNITED STATES PATENT AND TRADEMARK OFFICE
CERTIFICATE OF CORRECTION

PATENT NO.       : 7,588,557 B2                                  Page 1 of 1
APPLICATION NO.  : 10/670106
DATED            : September 15, 2009
INVENTOR(S)      : Naomi L. Nakao It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this

Twenty-first Day of September, 2010

David J. Kappos
*Director of the United States Patent and Trademark Office*